(12) United States Patent
Cueva-Méndez

(10) Patent No.: US 9,555,127 B2
(45) Date of Patent: Jan. 31, 2017

(54) SYSTEMS AND METHODS FOR DIMINISHING CELL GROWTH AND INDUCING SELECTIVE KILLING OF TARGET CELLS

(71) Applicants: Medical Research Council, Swindon (GB); Guillermo de la Cueva-Méndez, Madrid (ES)

(72) Inventor: Guillermo de la Cueva-Méndez, Madrid (ES)

(73) Assignees: Guillermo De La Cueva-Mendez, Madrid (ES); Medical Research Council, Swindon (GB)

( * ) Notice: Subject to any disclaimer, the term of this patent is extended or adjusted under 35 U.S.C. 154(b) by 0 days.

(21) Appl. No.: 14/345,138

(22) PCT Filed: Sep. 17, 2012

(86) PCT No.: PCT/EP2012/003881
§ 371 (c)(1),
(2) Date: Mar. 14, 2014

(87) PCT Pub. No.: WO2013/037504
PCT Pub. Date: Mar. 21, 2013

(65) Prior Publication Data
US 2014/0341930 A1 Nov. 20, 2014

(30) Foreign Application Priority Data
Sep. 15, 2011 (EP) .................................... 11007520

(51) Int. Cl.
| A61K 47/48 | (2006.01) |
| C12N 15/63 | (2006.01) |
| A61K 38/16 | (2006.01) |
| A61K 31/7088 | (2006.01) |
| C07H 21/02 | (2006.01) |
| C12N 15/113 | (2010.01) |

(52) U.S. Cl.
CPC ..... *A61K 47/48776* (2013.01); *A61K 31/7088* (2013.01); *A61K 38/164* (2013.01); *C07H 21/02* (2013.01); *C12N 15/63* (2013.01); *C12N 15/113* (2013.01); *C12N 2310/141* (2013.01); *C12N 2320/31* (2013.01); *C12N 2320/52* (2013.01)

(58) Field of Classification Search
None
See application file for complete search history.

(56) References Cited

U.S. PATENT DOCUMENTS

2009/0075270 A1* 3/2009 Cueva-Mendez et al. ....... 435/6
2014/0341930 A1* 11/2014 Cueva-Mendez .......... 424/172.1

FOREIGN PATENT DOCUMENTS

| EP | 2570134 A1 | * | 3/2013 |
| WO | WO0105421 | | 1/2001 |
| WO | WO 2013/037504 | * | 3/2013 |

OTHER PUBLICATIONS de la Cueva-Mendez et al, EMBO Journal, 2003, 22/2:248-251.*
Diago-Navarro et al, FEBS Journal, 2010, 277:3097-3117.*
Gabant et al, BioTechniques Apr. 2000, 28:784-788.*
Hu et al, International Journal of Microbiology vol. 2010, Article ID 781430, 10 pages doi:10.1155/2010/781430.*
Jensen et al, Molecular Microbiology, 1995, 17/2:205-210.*
Kamphuis et al J. Mol. Biol., 2006, 357:115-126.*
Lopez-Villarejo et al, Plasmid 67 (2012) 118-127.*
Monti et al, Nucleic Acids Research, 2007, vol. 35, No. 5 1737-1749.*
Munoz-Gomez et al, J. Bacteriology, May 2005, 187/9:3151-3157.*
Ruiz-Echevarria et al, J. Mil. Biol., 1995, 247:568-577.*
Ruiz-Echevarria et al, Molecular Microbiology, 1991, 5/11:2685-2693.*
Ruiz-Echevarria et al Mol. Gen. Genet., 1995, 248:599-609.*
Citation: Smith AB, López-Villarejo J, Diago-Navarro E, Mitchenall LA, Barendregt A, et al. (2012) A Common Origin for the Bacterial Toxin-Antitoxin Systems parD and ccd, Suggested by Analyses of Toxin/Target and Toxin/Antitoxin Interactions. PLoS ONE 7(9): e46499. doi:10.1371/journal.pone.0046499.*
Preston et al, ACS synthetic biology, (Aug. 10, 2015). Electronic Publication Date: Aug. 10, 2015 Journal code: 101575075. E-ISSN: 2161-5063. L-ISSN: 2161-5063.*
Pimentel et al, The EMBO Journal (2005) 24, 3459-3469.*
Kamphuis et al, Protein & Peptide Letters, 2007, 14:113-124.*
Shi, Y. et al, "[ReIE toxin protein of *Mycobacterium tuberculosis* induces growth inhibition of lung cancer A-549 cell].", U.S. Library of Medicine, XP002671017, database ascension No. NLM18575317, & Sichuan Da Xue Bao. Yi Xue Ban = Journal of Sichuan University. Medical Science Edition May 2008, LNKD PubMed: 18575317, 39:3:368-372, (May 2008).
Korch, S. et al, "Three *Mycobacterium tuberculosis* Rel toxin-antitoxin modules inhibit mycobacterial growth and are expressed in infected human macrophages", Journal of Bacteriology, 191:5:1618-1630, XP055021065, (Dec. 29, 2008).

(Continued)

*Primary Examiner* — Nita M Minnifield
(74) *Attorney, Agent, or Firm* — McHale & Slavin, P.A.

(57) ABSTRACT

The invention relates to a biological system for diminishing cell growth or inducing selective killing of target cells, in particular pathogenic bacterial or fungal cells, or cancer cells. The biological system is based on toxin-antitoxin systems, as found in prokaryotic plasmids and their host chromosomes. The biological system comprises a vehicle with a first nucleic acid sequence or amino acid sequence encoding for a prokaryotic toxin of a prokaryotic toxin-antitoxin pair, and a second nucleic acid sequence or amino acid sequence encoding for the corresponding prokaryotic antitoxin of the prokaryotic toxin-antitoxin pair. The system is characterized in that the toxin and/or the antitoxin is operably linked to a protein output modifier (POM) that comprises a nucleic acid sequence or amino acid sequence that modifies the relative rate of transcription, mRNA stability, mRNA translatability or protein stability of the toxin and/or antitoxin.

20 Claims, 22 Drawing Sheets

(56) References Cited

OTHER PUBLICATIONS

Nehlsen, K. et al, "Toxin-antitoxin based transgene expression in mammalian cells", Nucleic Acids Research, 38:5: E32-E32, XP055021115, (Dec. 8, 2009).
Correia, F. et al, "Kinase activity of overexpressed HipA is required for growth arrest and multidrug tolerance in *Escherichia coli*", Journal of Bacteriology, 188:24:8360-8367, XP055021132, (Oct. 13, 2006).
Picardeau, M. et al, "The spirochetal chpK—chromosal toxina??antitoxin locus induces growth inhibition of yeast and mycobacteria", FEMS Microbiology Letters, 229:2:277-281, XP055021136, (Dec. 1, 2003).
Yamaguchi, Y. et al, "Toxin-antitoxin systems and bacteria in Archaea", Annual Review of Genetics, 45:1:61-79, XP055020998, (Dec. 15, 2011).
Audoly, G. et al, "Effect of Rickettsial toxin VapC on its Eukaryotic host", Plos One, 6:10:E26528, XP055021120, (Oct. 27, 2011).
Thomas, M. et al, "Bridge-1, a novel PDZ-domain coactivator of E2A-mediated regulation of insulin gene transcription", Molecular and Cellular Biology, 19:12:8492-8504, (Dec. 1999).
Giallourakis, C. et al, "A molecular-properties-based approach to understanding PDZ domain proteins and PDZ ligands", Genome Research, vol. 16, pp. 1056-1072, retrieved Internet article: http://www.genome.org/cgi/doi/10.1101/gr.528206, (2006).

\* cited by examiner

A  Differential protein stability and selective cell killing

B  Differential mRNA stability and selective cell killing

A    Plasmids used in the experiment

B    293T cells 48h after co-transfection with indicated plasmids from A pUC18-PDZ$_2$FLAGKis-IRES-Kid18

SYSTEMS AND METHODS FOR DIMINISHING CELL GROWTH AND INDUCING SELECTIVE KILLING OF TARGET CELLS

CROSS REFERENCE TO RELATED APPLICATIONS

This is a national stage filing in accordance with 35 U.S.C. §371 of PCT/EP2012/003881, filed Sep. 17, 2012, which claims the benefit of the priority of European Patent Application No. 11007520.7, filed Sep. 15, 2011, the contents of each are incorporated herein by reference.

TECHNICAL FIELD

The present invention relates to a biological system for diminishing cell growth or inducing selective killing of target cells, in particular pathogenic bacterial or fungal cells, or cancer cells. The invention also relates to a pharmacological composition to be used in the treatment of such pathogenic diseases. The biological system according to the invention can be used in the treatment of a pathological bacterial or fungal disease or cancer. The invention further relates to the use of a biological system for therapy of a pathological condition, diagnostics, theranosis, drug discovery, Screening, creating animal models, target molecule identification and validation. In a further aspect, the invention also relates to a drug delivery system for delivering a vehicle to target cells by means of biologically-derived nanocells (minicells). The invention also relates to a method for delivery of a substance to target cells. The biological system according to the invention is based on toxin-antitoxin systems, as found in prokaryotic plasmids and their host chromosomes.

BACKGROUND ART

Prokaryotic toxin-antitoxin systems play a major role in the maintenance of genetic information and in response to stress. The toxin of a toxin-antitoxin pair has cytostatic capabilities and usually affects cell growth or leads to cell death. The toxin and its activity can be neutralized in cells containing a plasmid that encodes for the corresponding antitoxin for the toxin. Toxin-antitoxin systems thus contribute to the maintenance of the extrachromosomal genetic information in bacterial populations by interfering selectively with the growth or viability of plasmid-free segregants or of host cells that are about to produce plasmid-free segregants if their growth is not arrested. Such systems are also found in the chromosomes of bacteria and archaea where they can have different functions, such as regulation of cell growth and viability under different stress conditions.

The Kid-Kis toxin-antitoxin system of the plasmid R1 shows significant similarities with other existing toxin-antitoxin systems (Diago-Navarro et al., FEBS Lett 277, 3097-3117 (2010)). This toxin-antitoxin pair is encoded by the parD locus of the *Escherichia coli* plasmid R1, which is conserved in closely related plasmids like R100. In addition, there are also chromosomal homologues in *Escherichia coli*, which are functionally and structurally related to other known toxins-antitoxins. For the toxin-antitoxin pair Kid and Kis it was shown that the Kid toxin could specifically inhibit cell proliferation and viability in eukaryotic cells (De la Cueva Mendez et al., EMBO J 22, 246-251 (2003)). When both genes for the toxin Kid and the antitoxin Kis are expressed, the cells grow in a normal manner. If the concentration of the Kid toxin exceeded a certain ratio to the concentration of the Kis antitoxin or if the antitoxin gene expression was repressed, growth was inhibited and the cells subsequently died by apoptosis as a result of the Kid activity. Similar results were also reported for other toxin-antitoxin pairs (Kristoffersen et al., Appl Environ Microbiol 66, 5524-5526 (2000); Yamamoto T A et al., FEBS Lett 519, 191-194 (2002)).

The observation that toxin-antitoxins can be used for selective cell killing or diminishing cell growth in prokaryotic or eukaryotic cells makes toxin-antitoxin systems suitable for treatment of degenerative disorders, such as cancer.

US 2009/0075270 A1 describes methods for evading the action of *Escherichia coli* Kid (PemK), and for manipulating nucleic acid expression. In particular, target sites for Kid/PemK endoribonuclease were identified and mutated.

The US 2009/0124012 A1 describes compositions and methods for regulating cell growth and metabolism by expression of components of toxin-antitoxin pairs. The described system is used for decreasing the cellular growth rate and comprises a first nucleotide sequence encoding an mRNA interferase operably linked to a first heterologous regulatory element, wherein the expression of the nucleotide sequence diminishing the growth rate of the target cells.

EP 1 198 239 B1 describes a composition comprising the parD Kid toxin and parD Kis antitoxin, for use in a therapeutic method of inhibiting cell proliferation and/or cell cycle progression carried out on a human or animal body. The method comprises providing within eukaryotic cells in the human or animal body the toxin and antitoxin, under appropriate control for selective cell cycle inhibition and/or killing of target cells.

The ParD system has also been used to investigate a role of germ line in the sex differentiation in zebra fish during somatic development. The expression of Kid toxin eliminated selectively primordial germ cells, whereas the uniform expression of the Kis antitoxin protected somatic cell lines (Slanchev K et al., Proc Natl Acad Sci USA 102, 4074-4079 (2005)).

Although the observations that toxin-antitoxin essentially could be used for diminishing the cell growth rate or cell killing in both prokaryotic and eukaryotic cells, no approach or system has been described so far that could be applied to successfully treat a pathological disease by specifically killing pathologic prokaryotic or eukaryotic cells. It would hence be desirable to selectively kill target cells, cancer cells for instance, by a toxin-antitoxin combination in order to treat pathological conditions. In order to achieve this goal, it would be necessary to specifically target cells (e.g. pathologically affected cells) with a toxin-antitoxin combination in order to increase the concentration of the toxin over the antitoxin in the target cells for killing or to increase the concentration of the antitoxin in non-target cells to protect them from the activity of the toxin. Alternatively, the expression of the antitoxin could be repressed in order to obtain an excess of the toxin in the target cell.

Shi Ya-Li et al., US National Library of Medicine (NLM), Bethesda, Md., US (May 2008), RelE toxin protein of *Mycobacterium tuberulosis* induces growth inhibition of lung cancer A-549 cell) teaches RelE, RelB and RelE genes subcloned into PcDNA3. The recombinant vectors were used to transfect lung cancer A-549 cells by liposome transfection. Said genes were under the control of a heterologous promoter. This expression system, however, does not allow the controlled alteration of the ratio of an toxin/antitoxin pair within target and/or non-target cells. A similar expression system for Rel proteins is also disclosed in S. B.

Korch et al., Three *Mycobacterium tuberculosis* Rel Toxin-Antitoxin Modules inhibit mycobacterial growth an dare expressed in infected human macrophages, Journal of Bacteriology, Vol. 191, No. 5, Dec. 29, 2008.

Also other publications merely address the issue of cell growth inhibition by expressing or inhibiting the a toxin and/or an antitoxin of a toxin-antitoxin pair in target cells, but do not address the actual ratio of toxin/antitoxin within the target-cells and/or non-target cells (see K. Nehlsen et al., Toxin-antitoxin based transgene expression in mammalian cells, Nucleic Acids Research, Vol. 38, No. 5, Dec. 8, 2009; F. F. Correia et al., Kinase activity of overexpressed HipA is required for growth arrest and multidrug tolerance in *Escherichia coli*, Journal of Bacteriology, Vol. 199, No. 24, Oct. 13, 2006K; Mathieu Picardeau et al., The spirochetal chpK-chromosomal toxin and antitoxin locus induces growth inhibition of yeast and mycobacteria, FEMS Microbiology Letters, Vol. 229, No. 2, Dec. 1, 2003).

Another problem that needs to be faced is that the toxin-antitoxin members must be specifically delivered to the targeted cells in order to express their function or activity specifically in these cells. Different approaches have been employed for aiming a specific delivery of drugs, chemicals and other compounds to target cells, among these are viruses, plasmids, polymer particles or nanocells. These delivery systems are able to carry cell cycle inhibitors to the targeted cells while avoiding toxicity to non-targeted cells. Bacterially-derived minicells have been described for targeted delivery of chemotherapeutic drugs (Mac Diarmid et al., Cancer Cell, 11, 431-445 (2007)). Minicells were first observed and described by Howard Adler and colleagues in 1967 who also created the term "minicell" for bacterially-derived nanocells. Minicells are non-living nano-sized cells (approximately 200-400 nm in diameter) and are produced as a result of mutations in genes that control normal bacterial cell division, thereby de-repressing polar sides of cell division. Since the size of the vector is 200-400 nm in diameter, the term "nanocell", as used in the present invention, is often used instead of the term "minicell".

It was demonstrated that a range of chemotherapeutic drugs with differing structure, charge, hydrophobicity and solubility such as 5-fluoracil, carboplatin, cisplatin, doxorubicin, irinotecan, paclitaxel and vinblastine could be readily packaged within the minicells. Although the potency of minicells to deliver chemotherapeutic drugs to target cells constitutes a promising approach, specificity and cell targeting still remains as a problem. MacDiarmid et al delivered minicells to cancer cells using bispecific antibodies. The problem however was that the utilized antibodies were difficult and costly to prepare. Thus, bispecific antibodies did not provide the results that would be satisfactory for therapy or diagnosis.

It would therefore by desirable to have a nanocell-based delivery system by which not only toxin-antitoxin compounds could be transported to the respective target cells, but also any other drug, antigen, chemical, protein or whatsoever that needs to be delivered to pathological cells.

A further problem that needs to be faced is the immunogenicity of the nanocells since they are of bacterial origin. So far, a systemic administration could result in unwanted side-effects as bacterial products are known to elicit potent inflammatory responses activated by bacterial proteins and structures. A separation procedure has been developed to eliminate free endotoxin and free bacterial components to minimize the potential of toxic side-effects (MacDiarmid et al., Cancer Cell, 11, 431-445 (2007)).

DISCLOSURE OF INVENTION

Against this background, it is an object of the present invention to provide toxin-antitoxin-based systems and methods, which allow for specifically diminishing cell growth and/or selective cell killing in target cells whereas non-target cells are protected from the treatment. A further object of the invention is to provide a drug (or cancer cell imaging marker) delivery system, which allows to specifically deliver potent agents to target cells based on prokaryotically-derived nanocells.

The solution is provided by the invention as defined in the accompanying patent claims. Preferred embodiments are the subject of the sub-claims.

The present invention is based on the general concept of regulation and/or modulation the ratio between the toxin and the antitoxin of a prokaryotic toxin-antitoxin pair within target cells and/or in non-target cells.

The term "target cells" as used in the context of this invention refers to cells that are treated with a toxin-antitoxin construct according to the invention, and that are targeted to diminish the cell growth rate of these cells or to kill them. In the target cells either the activity of the toxin is increased relative to the activity of the antitoxin, or the activity of the antitoxin is decreased relative to the activity of the toxin.

The term "non-target cells" as used in the context of this invention refers to cells that are treated with a toxin-antitoxin construct according to the invention, and that are targeted for protection against the toxic effects of the toxin of the toxin-antitoxin pair that diminishes the cell growth rate of these cells or kills them. In the non-target cells either the activity of the toxin is decreased relative to the activity of the antitoxin, or the activity of the antitoxin is increased relative to the activity of the toxin.

A "targeted cell" is a cell that was effectively treated with a toxin-antitoxin construct of the invention, whereas a "non-targeted cell" is a cell that remained unaffected from the treatment.

In order to exhibit cytotoxic effects on target cells, it is necessary to either specifically kill the target cells or to protect non-target cells from the toxic effect of the toxin. The present invention utilizes a protein output modifier (POM) that is able to change the relative ratio in the concentration of the toxin and/or the antitoxin within the target cells and/or, where applicable, within non-target cells. Preferably the POM utilized in the present invention is cell-specific, which is herein also termed as cs-POM (cell-specific protein output modifier). The protein output modifier (POM) according to the invention can be any compound or molecule that is able to change the concentration of the toxin-antitoxin substance within the targeted cell, either on the level of DNA, RNA or protein. In this respect, the protein output modifier (POM) modifies the relative rate of transcription, mRNA stability, mRNA translation stability or protein stability of the toxin and/or antitoxin. Depending on the kind of protein output modifier (POM) used, the level of modulation can be different and either affect transcription, translation or the stability of mRNA or the synthesized protein within the cell.

Diminishing cell growth or cell killing of target cells can hence be achieved by changing the relative ratio in the concentration of the toxin and/or the antitoxin, either in the target cells and/or in the non-target cells. There are several alternatives of how such a change in the ratio of the toxin relative to the antitoxin can be achieved. In one aspect the active antitoxin output within the cell can be decreased in the target cells, which would lead to an excess of the toxin over the antitoxin in the target cells, thereby inducing cell death or cell growth arrest. In addition or alternatively, the antitoxin output can be increased in the non-target cells relative to the toxin output, which would result in a protection of the non-target cells. In another aspect, the toxin output in the non-target cells can be decreased relative to the antitoxin output, resulting in a protection of the non-target cells. As a further alternative, the toxin output in the target cells can be increased, which would necessarily result in a killing of the target cells. Therefore, either killing of the target cells or protection of the non-target cells can be used as an approach for diminishing cell growth or inducing selective killing of pathogenic cells.

In order to achieve a change in the relative ratio in the concentration of the toxin and/or the antitoxin within the target cells and/or where applicable within the non-target cells, the biological system according to the invention comprises a vehicle with the first nucleic acid sequence or amino acid sequence encoding for a prokaryotic toxin of a prokaryotic toxin-antitoxin pair, and a second nucleic acid or amino acid sequence encoding for the corresponding prokaryotic antitoxin of the prokaryotic toxin-antitoxin pair. The biological system according to the invention can thus be a nucleic acid or a polypeptide/protein. The invention is characterized in that the toxin and/or the antitoxin is operably linked (preferably covalently linked) to a protein output modifier (POM) that comprises a nucleic acid sequence or amino acid sequence that modifies the relative rate of transcription, mRNA stability, mRNA translatability or protein stability of the toxin and/or antitoxin, thereby changing the relative ratio in the concentration of the toxin and/or the antitoxin within the target cells and/or within non-target cells.

The protein output modifier (POM) is operably linked to the toxin and/or the antitoxin can be any molecule or compound that modulates the output of the toxin and/or antitoxin within the target cells and/or non-target cells. Ideally, POM is a DNA, RNA or amino acid sequence functionally linked to the toxin and/or the antitoxin gene or protein. The POM interacts in a cell-specific manner and utilizes toxic antitoxin/toxin ratios in the target cells and protective antitoxin/toxin ratios in the non-target cells. Therefore, the protein output modifier (POM) can be any molecule selected from the group consisting of promoter/operator sequence(s), miRNAs target site(s), 3'-UTRs or ubiquitin ligase target domain(s) that results in a specific alteration of the ratio of the toxin-antitoxin within in the target cells and/or non-target cells. Preferably any protein domain that could lead to protein instability or any RNA domain that could lead to mRNA instability could be used in the present invention.

It is preferred that the strategy is based on the linkage of the toxin and/or the antitoxin to one or more protein output modifier (POM) targeted by one or more cellular POM interacting molecule that are (over)expressed in the target cells and/or, if applicable, in non-target cells, and that interacts with the one or POM linked to these genes/proteins, thereby resulting in a decrease of the toxin outputs in the non-target cells and/or decrease of the antitoxin outputs in the target cells, or an increase of the toxin outputs in the target cells and/or increase of the antitoxin outputs in the non-target cells. In many pathologic cells, in particular cancer cells, certain mRNAs and proteins are higher expressed than in normal cells and therefore these molecules are suitable targets for drugs. For example, the protein output modifier (POM) can contain one or more PDZ domains from HR-HPV-E6 target cellular proteins, wherein the cellular POM interacting molecule is the E6 oncogene from high risk HPV serotypes that interacts with said PDZ domain(s). The presence of E6 oncogene in cells results in ubiquitination and degradation of PDZ-Kis and thus apoptosis of cells that express PDZ-Kis, Kid and HR-HPV E6. Only in cells that express E6, the PDZ-Kis is destroyed, resulting in an excess of the toxin Kid relative to the antitoxin Kis in the cells.

miRNAs are micro-RNAs (sometimes also termed as miRNAs), i.e. highly conserved non-coding RNAs that are post-transcriptional regulators binding to complementary sequences on target messenger RNA transcripts (mRNA). Binding of miRNA to the complementary mRNA usually results in a translational repression of the target molecule or gene silencing. miRNAs are either produced from own genes or from introns. The major miRNA is part of an active RNA-induced silencing complex (RISC) containing Dicer and other associated proteins. RISC is also known as a micro-RNA ribonucleoprotein particle (miRNP). Perfect or near perfect base pairing with the target mRNA promotes cleavage of the target mRNA, which is one mechanism of how miRNA can regulate gene regulation. At lower complementarity, miRNAs often inhibit protein translation of the target mRNA. miRNAs occasionally also cause histone acetylation modification and DNA methylation of promoter sites, which affects the expression of target genes.

In another preferred embodiment, the protein output modifier (POM) contains one or more miRNA target site(s) and the cellular POM interacting molecule is a miRNA that interacts with said miRNA target site(s). In a preferred embodiment a single target site is cloned, which fulfills the following conditions: i) being positioned immediately downstream of the gene to be downregulated (i.e. antitoxin in targeted cells or toxin in non-targeted cells) and ii) being 100% complementary to the POM interacting molecule of choice (i.e. a specific miRNA). Selectivity for that specific miRNA is significantly increased when these two conditions are fulfilled.

If the toxin or the antitoxin is linked to a POM that contains one or more miRNA target sequence(s), the resulting mRNA product interacts with the respective miRNA and, if there is high complementarity between the mRNA and the miRNA target sequence, causes cleavage of the construct. miRNA-TS (miRNA target sequence) fused to either a toxin or an antitoxin causes a destruction of either the toxin or antitoxin upon binding of the respective miRNA to the miRNA-TS. This changes the ratio of the toxin and/or antitoxin relative to the other member of the toxin-antitoxin pair. For example, if the Kid toxin is fused to a miRNA-TS, complementary miRNA that is overexpressed in a normal cell binds to the matched miRNA-TS and results in a destruction of the Kid toxin. A lower level of the Kid toxin in the cell relative to the Kis antitoxin causes protection of the non-targeted cell. A destruction of the antitoxin Kis in pathogenic cells, for example cancer cells, on the other hand, would result in an excess of the Kid toxin, thereby causing cell death of the so treated cell.

In another preferred embodiment, the protein output modifier (POM) contains a 3'-UTR sequence in the toxin or antitoxin nucleic acid sequence. A 3'-UTR (three prime untranslated region) is a section of mRNA that follows the coding region. 3'-UTRs very often contain regulatory sequences such as polyadenylation signals, binding sides for proteins that affect mRNA stability or location in the cell, or binding sides for miRNAs. 3'-UTRs therefore control translation of the respective mRNA. By linking a 3'-UTR sequence to either the toxin and/or the antitoxin, the stability of the protein output modifier (POM) and therefore the stability of the whole construct can be controlled.

Depending on the respective toxin-antitoxin pair that is employed in the present invention, the ratio between the antitoxin and the toxin required to induce toxicity or protection can vary. Toxin-antitoxin pairs that are derived from parD locus very often demand an excess of the toxin relative to the antitoxin. For example, Kid can kill cells if the ratio of copies between Kis and Kid is <0.5 in the target cells, or, non-target cells are protected if the ratio between Kis and Kid is ≥0.5. Depending on the toxin-antitoxin pair applied, the ratio between the antitoxin and toxin can be <1 in the target cells or a ≥0.5 in the non-target cells. In one embodiment, the ratio between the antitoxin and toxin is <0.5 in the target cells and/or a ≥0.5 in the non-target cells. In another embodiment the ratio between the antitoxin and toxin is <1 in the target cells and/or a ≥1 in the non-target cells.

In a preferred embodiment, the protein output modifier (POM) contains a promoter/operator sequence that increases the rate of transcription of the toxin in the target cells or decreases the rate of transcription of the antitoxin in the target cells, and/or decreases the rate of transcription of the toxin in the non-target cells or increases the rate of transcription of the antitoxin in the non-target cells.

Preferably, the toxin-antitoxin pair is selected from the group consisting of kid/kis, CcdB/CcdA, MazF/MazE, ChpBK/ChpBI, RelE/RelB, ParE/ParD, HipA/HipB, PhD/Doc, Hok/Sok, YafM/YoeB, YafN/YafO, YgjM/YgjN, YgiT/YgiU, DinJ/YafQ, VapB/VapC, HipB/HipA, HicB/HicA, and their homologs in other organisms. The invention is not restricted on these particular toxin-antitoxin pairs, but will also comprise any toxin-antitoxin pair which has the same activity and function as the ones already described.

Examples of known toxin-antitoxin pairs are described in Table 1:

tide/protein that carries a first nucleic acid sequence or amino acid sequence encoding for the prokaryotic toxin of a prokaryotic toxin-antitoxin pair, and the second nucleic acid sequence or amino acid sequence encoding for the corresponding prokaryotic antitoxin of the prokaryotic toxin-antitoxin pair. Preferably, the protein output modifier (POM), the prokaryotic toxin and the prokaryotic antitoxin are contained in a single or in independent carrier plasmids or viruses, wherein the toxin and antitoxin are transcribed from the same single promoter or from independent promoters.

When single promoters (i.e. bicistronic transcription) are used, toxin and antitoxin may be linked to each other using IRES or sequences encoding viral 2A self-cleaving peptides or derivatives of these such as described in Kim J H, Lee S-R, Li L-H, Park H-J, Park J-H, et al., High Cleavage Efficiency of a 2A Peptide Derived from Porcine Teschovirus-1 in Human Cell Lines, Zebrafish and Mice, PLoS One. 2011; 6(4):e18556. Epub 2011 Apr. 29.

The promoter can be a constitutive promoter or a controllable promoter and is located upstream of the toxin and/or antitoxin gene. In a preferred embodiment, the toxin and antitoxin are regulated by independent promoters, such that the copies of the toxin and/or antitoxin can be controlled in a cell-specific manner. Alternatively, regulation may take place by promoter activating elements that result in a higher or lower expression of the respective gene upon binding to promoter/operator sequences.

The biological system according to the invention can be used in the treatment of any pathological condition, including cancer, that induces or represses the expression of a POM modulating molecule, e.g. miRNA, E3 ubiquitin ligase, transcription factor etc. in affected cells as compared to non-affected cells. The changes may be induced by viral

TABLE 1

| Family | Operon | Toxin | Antitoxin | Source organism |
|---|---|---|---|---|
| ccdAB | ccdAB | CcdB | CcdA | *Escherichia coli*/plasmid |
| parDE | parDE | ParE | ParD | *Escherichia coli*/plasmid |
| phd/doc | phd/doc | PhD | Doc | Prophage P1 |
| mazEF | mazEF (chpAK) | MazF (ChpK) | MazE (ChpA) | *Escherichia coli*/chromosome |
|  | kis/kid (parD) | Kid | Kis | *Escherichia coli*/plasmid |
|  | pemIK | PemK | PemI | *Escherichia coli*/plasmid |
|  | ChpBIK | ChpBK | ChpBI | *Escherichia coli*/chromosome |
|  | mazEF$_{mt1}$-mazEF$_{mt7}$ | MazF$_{mt1}$-MazF$_{mt7}$ | MazE$_{mt1}$-MazE$_{mt7}$ | *Mycobacterium tuberculosis*/chromosome |
|  | mazEF$_{Sa}$ | MazF$_{Sa}$ | MazE$_{Sa}$ | *Staphylococcus aureus*/chromosome |
|  | pemIK$_{Sa}$ | PemK$_{Sa}$ | PemI$_{Sa}$ | *Staphylococcus aureus*/plasmid |
| relBE | relBE | RelE | RelB | *Escherichia coli*/chromosome/archaea |
|  | yefM-yoeB | YoeB | YafM | *Escherichia coli*/chromosome |
|  | yafNO | YafO | YafN | *Escherichia coli*/chromosome |
|  | ygjNM | YgjN | YgjM | *Escherichia coli*/chromosome |
|  | ygiUT (mqsRA) | YgiU (MqsR) | YgiT (MqsA) | *Escherichia coli*/chromosome |
|  | dinJ-yafQ | YafQ | DinJ | *Escherichia coli*/chromosome |
| higBA | higBA | HigB | HigA | *Vibrio cholerae*/chromosome |
| vapBC | vapBC | VapC | VapB | *Mycobacterium smegmatis* chromos./archaea |
| ζε | ζε | ζ | ε | *Streptococcus pyogenes*/plasmid |
| hipBA | hipBA | HipA | HipB | *Escherichia coli*/chromosome |
| hicAB | hicAB (yncN/ydcQ) | HicA (YncN) | HicB (YdcQ) | *Escherichia coli*/chromosome |

An example for a toxin-antitoxin pair that requires a ratio between the antitoxin and toxin <1 in the target cells and/or ≥1 in the non-target cells is the parD/parE system.

As an example, the following toxin-antitoxin modules require a ratio between the antitoxin and toxin <0.5 in the target cells and/or 0.5 in the non-target cells: ccdAB, PhD/Doc, mazEF family.

The vehicle as used in the present invention can be any molecule or compound, ideally a nucleic acid or polypeptide.

infection, for instance. Systems that express/repress certain levels of a POM interacting molecule do not only have potential for killing specific cells, but can also be used to influence development of the human or animal body, to create animal models for degenerative diseases or for developmental studies. POM interacting molecules can also be used to induce selection/counterselection of cells in genetic screens, in drug discovery, target identification and validation.

The present invention also relates to a pharmaceutical composition, comprising a vehicle with a first nucleic acid sequence or amino acid sequence encoding for a prokaryotic toxin of a prokaryotic toxin-antitoxin pair, and a second nucleic acid sequence or amino acid sequence encoding for the corresponding prokaryotic antitoxin of the prokaryotic toxin-antitoxin pair. The toxin and/or the antitoxin is/are operably linked, preferably covalently linked, to a protein output modifier (POM) that comprises a nucleic acid sequence or amino acid sequence that modifies the relative rate of transcription, mRNA stability, mRNA translatability or protein stability of the toxin and/or antitoxin thereby changing the relative ratio in the concentration of the toxin and/or the antitoxin within the target cells and/or, where applicable, within non-target cells by either decreasing the antitoxin outputs in the target cells (killing) and/or increasing the antitoxin outputs in the non-target cells (protection) relative to the toxin outputs, and/or by increasing the toxin outputs in the target cells (killing) and/or decreasing the toxin outputs in the non-target cells (protection) relative to the antitoxin outputs, and a pharmaceutical carrier.

Any suitable pharmaceutical carrier can be used for solubilisation and enhanced delivery. The use of nanocells (minicells) is particularly preferred. Any pathological condition of bacterial, fungal or viral origin, or cancer can be treated with the biological system according to the invention as long as a POM interacting molecule is (over)expressed or repressed in the respective target cell. Examples of conditions to be treated are tumors, psoriasis, meningitis, arteriosclerosis, and any viral, fungal, bacterial or parasitic infections in which killing of the infected host cell would impede spread of the pathogen or where killing of the pathogen itself may be an appropriate strategy.

The invention also relates to novel drug delivery system for delivering a biologically active substance to a target cell. Examples of substances to be delivered are any compounds or compositions such as drugs, chemicals, proteins, cell proliferation inhibitors or an antitoxin-toxin construct according to the invention. The nanocells are biotechnologically modified in order to minimize or exclude the risk of immunogenic and inflammatory responses in the host. Accordingly, the drug delivery system according to the invention comprises nanocells that are coated with one or more antibodies that recognize antigens specifically expressed by the target cells by exposing multiple copies of the Fc binding domain of Protein G, or protein A, protein A-G fusions, Fc-receptors (FcR), and those described in "Fc receptors and immunoglobulin binding factors" by Fridman W H (1991). The FASEB Journal, 5: 2684-2690 and in "FcRn: the neonatal Fc receptor comes of age" by Roopenian D C and Akilesh S. (2007) Nature Reviews in Immunology, 7:715-725, and references therein, to the external medium.

In order to minimize or avoid unwanted immunogenic or inflammatory responses of the host, the nanocells are produced preferably from minCD$^-$/msbB$^-$ bacterial strains (or any other bacterial strain that lacks lipid A production). These cells do not produce lipidA (a potent immunostimulator of cytokine production in mammals), which normally causes immunological responses in the host such as increased TNF-alpha/beta production by macrophages and other blood cells. In another embodiment, other mutations are used to make minicells (e.g. minCD and minC and minCDE) and to make even less acylated lipidA variants (e.g. msbB, htrB etc).

In principle, any bacterial strain (also gram positive ones) can be used in the context of the present invention, which are lipid A minus.

Preferably, the Fc binding domain of Protein G is anchored to the outer membrane of the nanocells via an invasin protein fragment covering amino acids 1 to 796 of *Yersinia pseudotuberculosis*. This polypeptide has only low immunogenic properties and is therefore particularly suited for use in the drug delivery system of the invention. The Fc binding domain of Protein G is a polypeptide fragment containing aminoacids 191 to 384 of Streptococcal Protein G.

In other embodiments of the invention, anchoring of the Fc binding domain to the membrane may be achieved using invasin transmembrane domain (plus additional invasin domains that project it outside) or any other transmembrane domain fused to the Fc binding domain, such as protein A, protein A-G fusions, Fc-receptors (FcR), and those described in "Fc receptors and immunoglobulin binding factors" by Fridman W H (1991). The FASEB Journal, 5: 2684-2690 and in "FcRn: the neonatal Fc receptor comes of age" by Roopenian D C and Akilesh S. (2007) Nature Reviews in Immunology, 7:715-725, and references therein.

Nanocells that are coated with specific antibodies that bind to antigens expressed by the target cells are able to deliver the carried substance to the target cells. In addition, it is possible that nanocells are coated with binding molecules that bind to antigens that have therapeutic or diagnostic properties. As an example in which this approach might be useful is the binding of molecules that may facilitate internalization of the nanocell by the target cell, or that may induce/increase killing of the target cell even before nanocell internalization, or that may facilitate imaging of nanocells in vivo. This is for example useful for tumor imaging or to examine biodistribution of nanocells in vivo.

The drug delivery system according to the invention is suitable for use in therapy, diagnosis or theranosis. It is noteworthy that the drug delivery system of the invention can be used to carry any substance or molecule that is intended to be delivered to a target cell. The substance may be selected from the group consisting of chemicals, drugs, proteins, nucleic acids or combinations thereof. In a preferred embodiment, a biological system as described herein consisting of a prokaryotic toxin and/or antitoxin is delivered by the drug delivery system according to the invention.

The invention also relates to a method for delivery of a substance such as chemicals, drugs, proteins, nucleic acids or combinations thereof to target cells and comprises the steps of producing the substance in a nanocell parental bacterial strain and producing nanocells from said substance-producing parental bacteria cells, or incubating the substance with nanocells produced from parental bacteria cells, coating the nanocells with one or more antibodies that recognize antigens specifically expressed by said target cells by exposing multiple copies of the Fc binding domain of Protein G (or the ones described above) to the external medium, exposing the target cells to said nanocells. Therefore, the substance can be produced in the nanocell parental bacterial strain if the substance is a nucleic acid or a protein/polypeptide. Alternatively, nanocells produced from parental bacterial cells can be incubated with the substance to be delivered, so that such substance is internalized by nanocells.

BRIEF DESCRIPTION OF DRAWINGS

The invention is explained in more detail and illustrated in the accompanying Figures.
Figure Legends
FIG. 1. Cell-specific-Protein-Output-Modifiers (cs-POMs) are protein expression regulatory elements that induce high toxin-antitoxin ratios in targeted cells (killing them) but still maintain these ratios low in other cell types (to protect them from toxicity).

Toxin Kid induces proliferation arrest and apoptosis in human cells, and antitoxin Kis protects from these effects. Each molecule of Kis neutralizes two molecules of Kid. Therefore, Kid/Kis ratios >2 induce cell killing, whilst Kid/Kis ratios ≤2 protect cells from the deleterious effect of Kid. A cs-POM is a protein expression (or proteins stability) regulatory element that induces Kid/Kis values higher than 2 in specific (targeted) cells, killing them, whilst maintaining Kid/Kis values ≤2 in other (non-targeted) cells, protecting them from toxicity. Cell specific killing may be achieved using cs-POMs that change Kis (A) or Kid (B) relative levels, differentially, in targeted and non-targeted cells. cs-POMs may be used that either decrease the relative levels of Kis in targeted cells or increase them in non-targeted cells (A). Alternatively, cs-POMs may be exploited to either increase the relative levels of Kid in targeted cells or to decrease them in non-targeted cells (B). cs-POMs may exert their function at different stages within the central dogma of gene expression. Accordingly, cs-POMs may influence the relative rate of transcription of kis and kid genes, the stability/translatability of kis and kid mRNAs, or the stability of their encoded proteins, in a cell-specific manner (C). Therefore, several cs-POMs may be used in combination to exert an even tighter control of the relative Kis and Kid outputs in targeted and non-targeted cells.

Scheme depicting the mode of action of cs-POMs decreasing the stability of protein Kis (A) or of its encoding mRNA (B) in targeted cells, but not in non-targeted cells. (A) cs-POM is a protein domain fused to Kis that is ubiquitylated by an E3 ubiquitin ligase (i.e. tagged for degradation by the proteosome) exclusively in targeted cells. This results in degradation of Kis (and induction of Kid toxicity) in such cells, but not in the rest of cells. (B) cs-POM is a DNA sequence 100% complementary to an miRNA highly expressed in targeted cells but not very abundant in non-targeted cells. This reduces the stability of kis-mRNA (and therefore Kis outputs) in targeted cells, killing them without affecting non-targeted cells.

Figure 1:
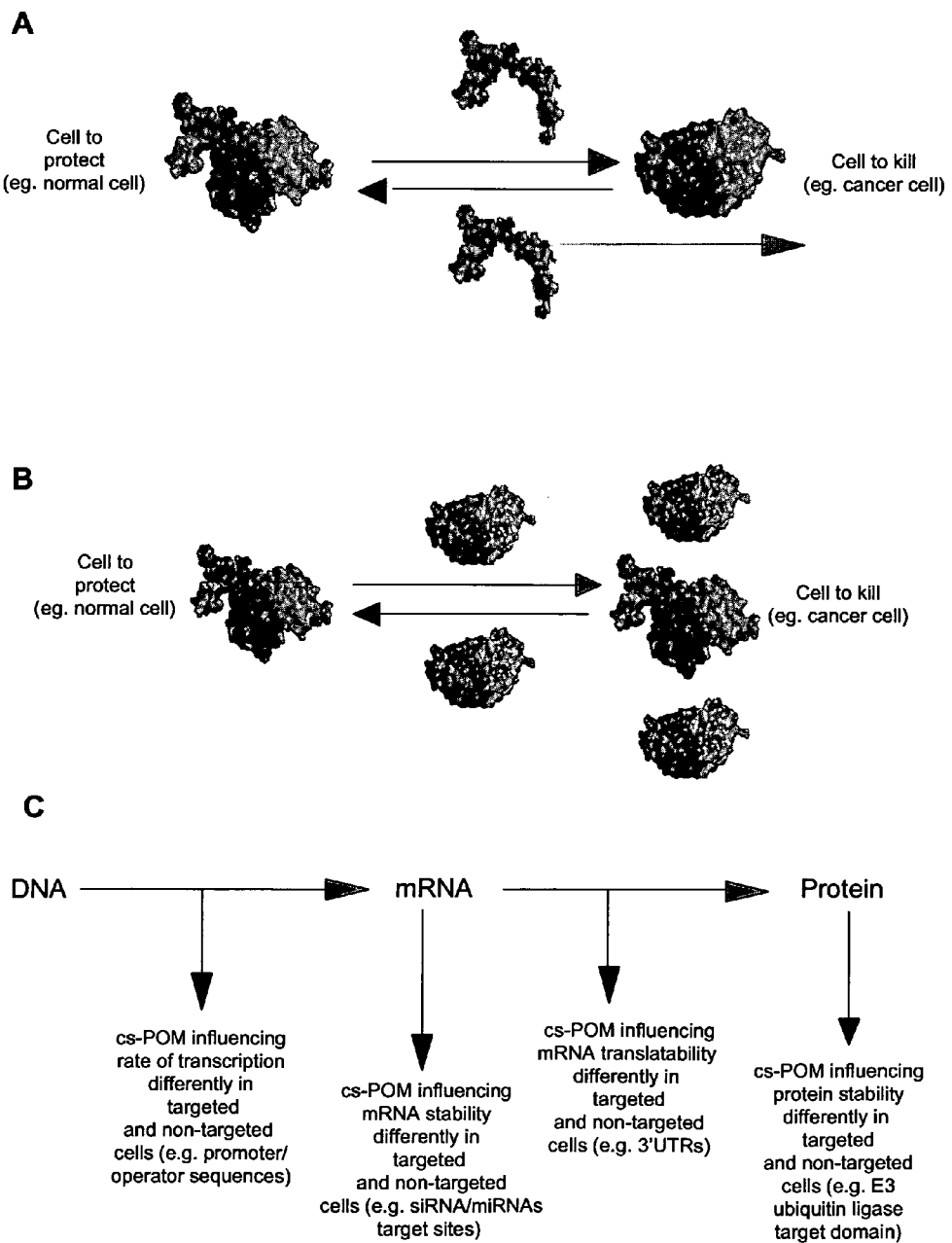
Figure 2:
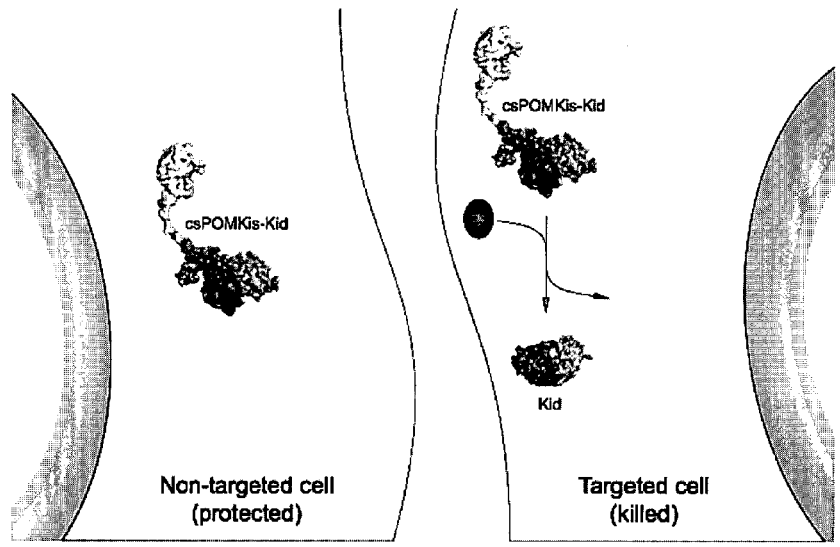
FIG. 2. cs-POMs may function by controlling protein or mRNA stability differentially in targeted and non-targeted cells.
Figure 2:
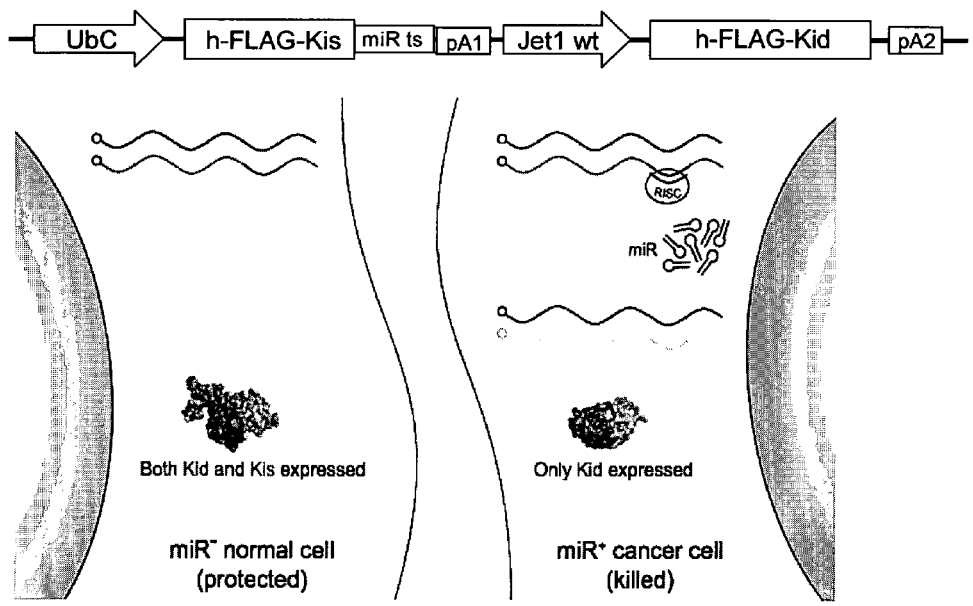
Figure 3:
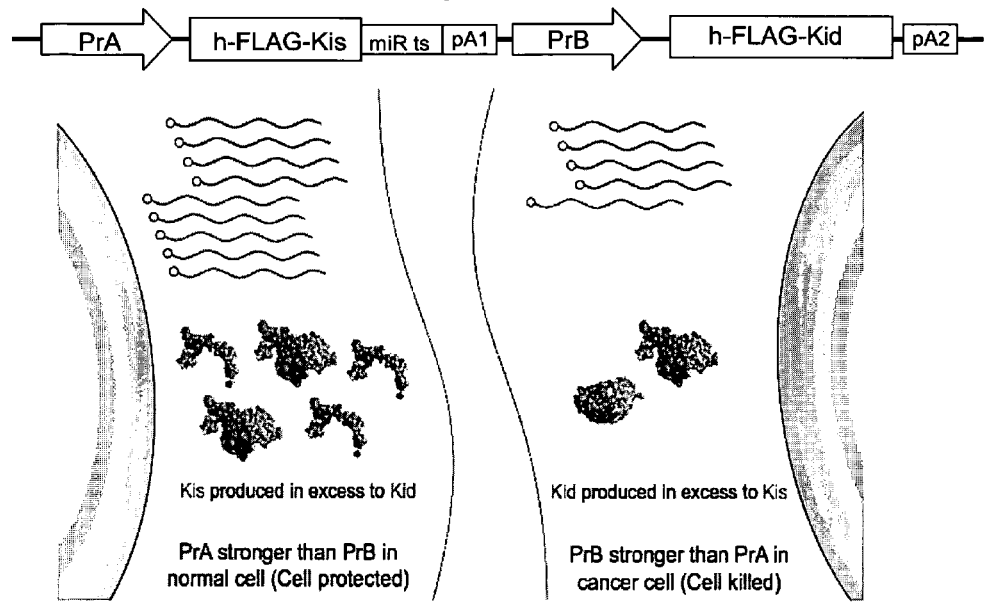
Figure 3:
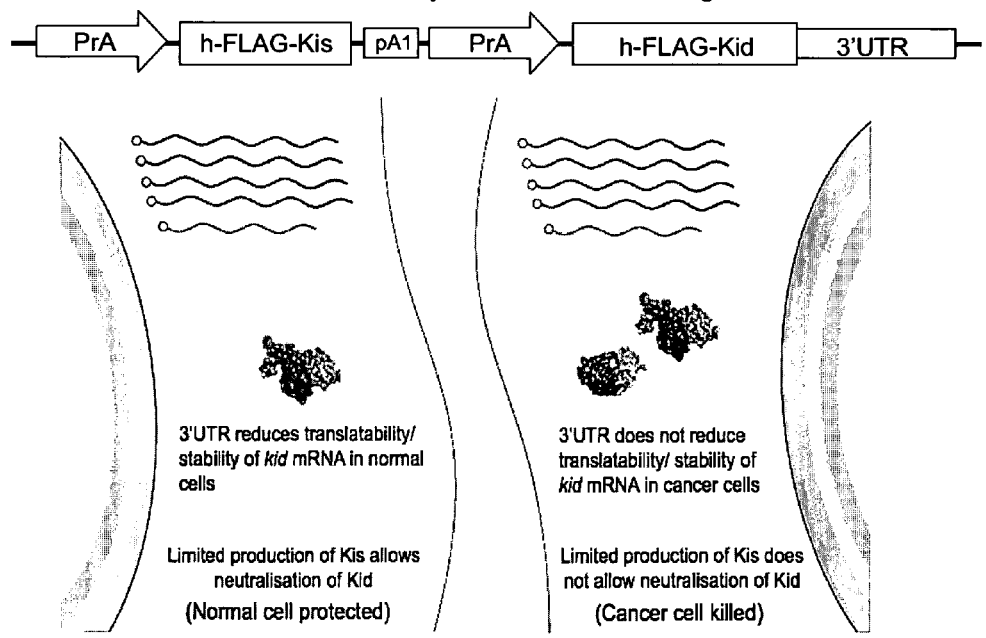

FIG. 3. cs-POMs may function by controlling transcription of translation rates differentially in targeted and non-targeted cells.

Scheme depicting the mode of action of cs-POMs affecting the relative rate of transcription (A) or of translation (B) of kid or kid genes in targeted and non-targeted cells. (A) cs-POM is a promoter/operator element that ensures high transcriptional rates of kis in non-targeted cells but very low in targeted cells, compared to a reference promoter/operator used to transcribe kid in both types of cells. Therefore only non-targeted cells can produce enough Kis to neutralize Kid. Alternatively, the promoter/operator element may function by inducing relatively high transcriptional rates of Kid in targeted cells, but very low in non-targeted, compared to a reference promoter/operator used to transcribe kis in both types of cells (not illustrated). (B) cs-POM is a 3'-UTR sequence decreasing the translatability of kid-mRNAs, compared to that of kis-mRNAs, in non-targeted cells, but not in targeted cells. Alternatively the 3'-UTR may decrease the translatability of kis-mRNA, compared to that of kid-mRNAs, in targeted cells, but not in non-targeted cells, (not illustrated).

Figure 4:
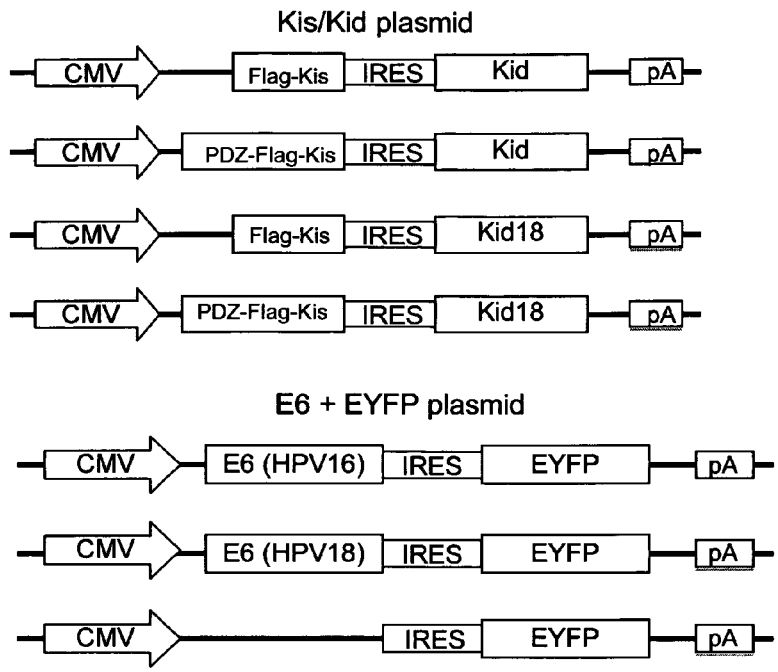
Figure 4:
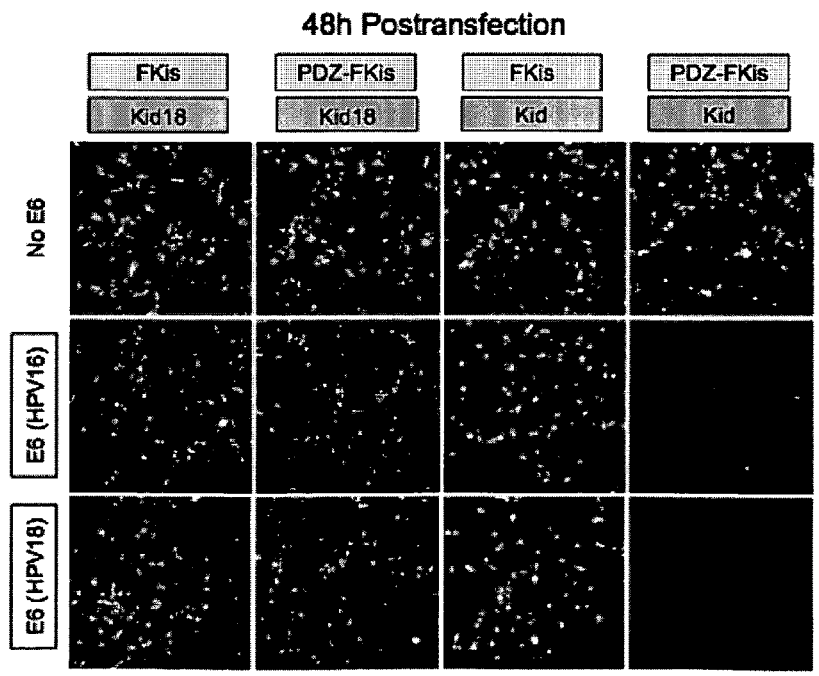

FIG. 4 PDZ domains from human MAGI-1 function as cs-POMs that enable protection from Kid toxicity only if cells do not express HR-HPV oncogene E6.

A set Kis/Kid-expressing plasmids and YEFP expressing plasmids were made as depicted in (A). In the Kis/Kid group, four plasmid variants were made, which expressed either wildtype Kis or this protein fused to residues 293-733 from human MAGI-1 protein (which includes two PDZ domains known to be targeted by oncogene E6 to induce degradation of MAGI-1 in HPV infected cells), and either wildtype Kid or a non-toxic mutant of this protein (Kid18). In the YEFP group, three variants were made, one expressing the fluorescent protein alone or together with oncogene E6 from high risk HPV serotypes 16 and 18. In both plasmid sets co-expression of Kis and Kid variants or of EYFP and E6 from the same promoter was facilitated using a bicistronic operon containing an internal ribosome entry site (IRES) between gene pairs. To obtain a bicistronic construct in eukaryotes, other alternatives may be used, such as sequences encoding viral self-cleaving 2A peptides and its derivatives (eg those described in Kim J H, Lee S-R, Li L-H, Park H-J, Park J-H, et al. (2011) High Cleavage Efficiency of a 2A Peptide Derived from Porcine Teschovirus-1 in Human Cell Lines, Zebrafish and Mice. PLoS ONE 6(4): e18556. doi:10.1371/journal.pone.0018556). (B) All possible 1:1 combinations of plasmids from each set was used to transfect 293T cells, and numbers of YEFP-positive cells in these samples were analyzed 48 hours post-transfection. This analysis revealed that YEFP-positive cells cannot be observed when PDZ-Kis, Kid and E6 are co-expressed, but are detected in all other cases (i.e. when either PDZ cs-POM, E6 or Kid activity are absent from that combination).

Figure 5:
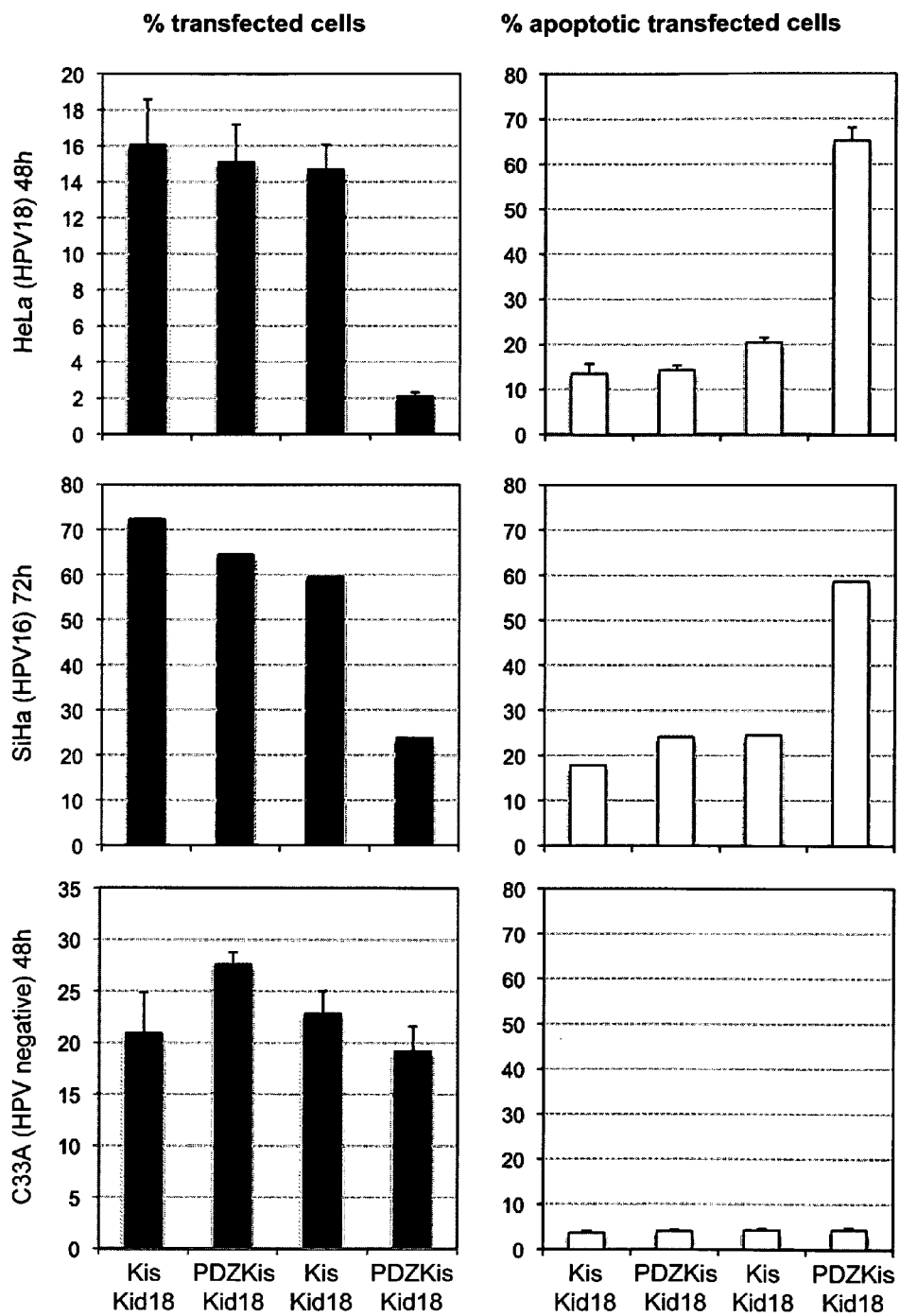

FIG. 5. PDZKisKid induces apoptosis in HPV-positive cancer cell lines, but not in HPV-negative control cells Cervical cancer cell lines HeLa (HPV18 positive), SiHa (HPV16 positive) as well as a control cell line (C33A; HPV negative) were co-transfected with each one of the Kis/Kid expressing plasmids depicted in FIG. 4, plus the YEFP-only (i.e. no E6) shown in the same figure. Transfected (i.e. fluorescent) cells, as well as apoptotic (i.e. annexin-V-positive) cells amongst these, were measured by flow cytometry at the time indicated in the figure. Transfection of HeLa and SiHa (but not C33A) cells with the PDZKisKid-expressing plasmid (but not with any of the other plasmids) results in lower number of fluorescent cells, as well as in a simultaneous increase in numbers of apoptotic transfected cells.

Figure 6:
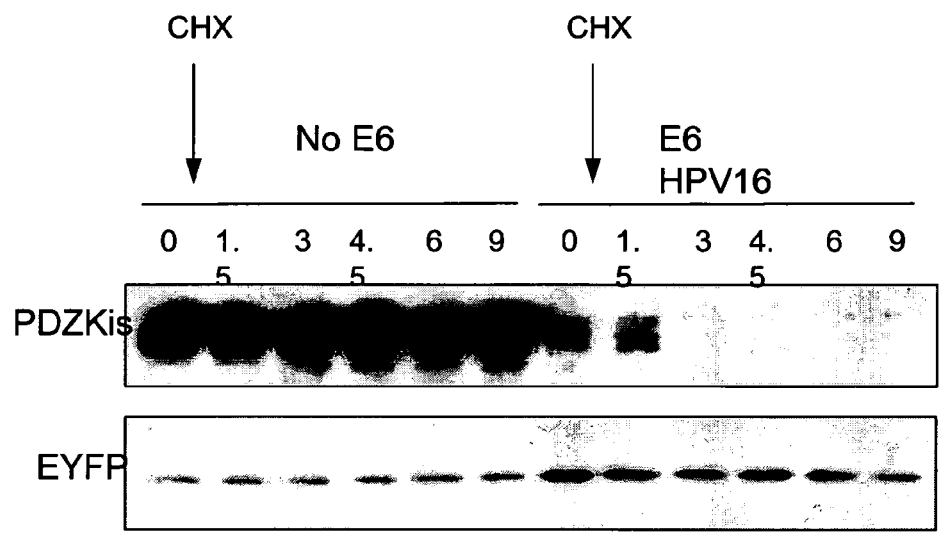

FIG. 6. E6 reduces the half-life of PDZKis in human cells

Western blot analysis of whole protein extracts from 293T cells co-transfected with a plasmid expressing PDZKis and either the plasmid expressing YEFP alone (left panels) or YEFP plus E6 from HPV16 (right panels) depicted in FIG. 4. Extracts were prepared before and at different time points after addition of cyclohexamide to inhibit new protein synthesis, and the relative abundance and half life of PDZ-Kis previously present in these extracts was determined using antibodies against PDZKis and control protein YEFP. The analysis revealed that stability of PDZKis is severely reduced in cells expressing E6, compared to cells where the oncogene is absent.

Figure 7:
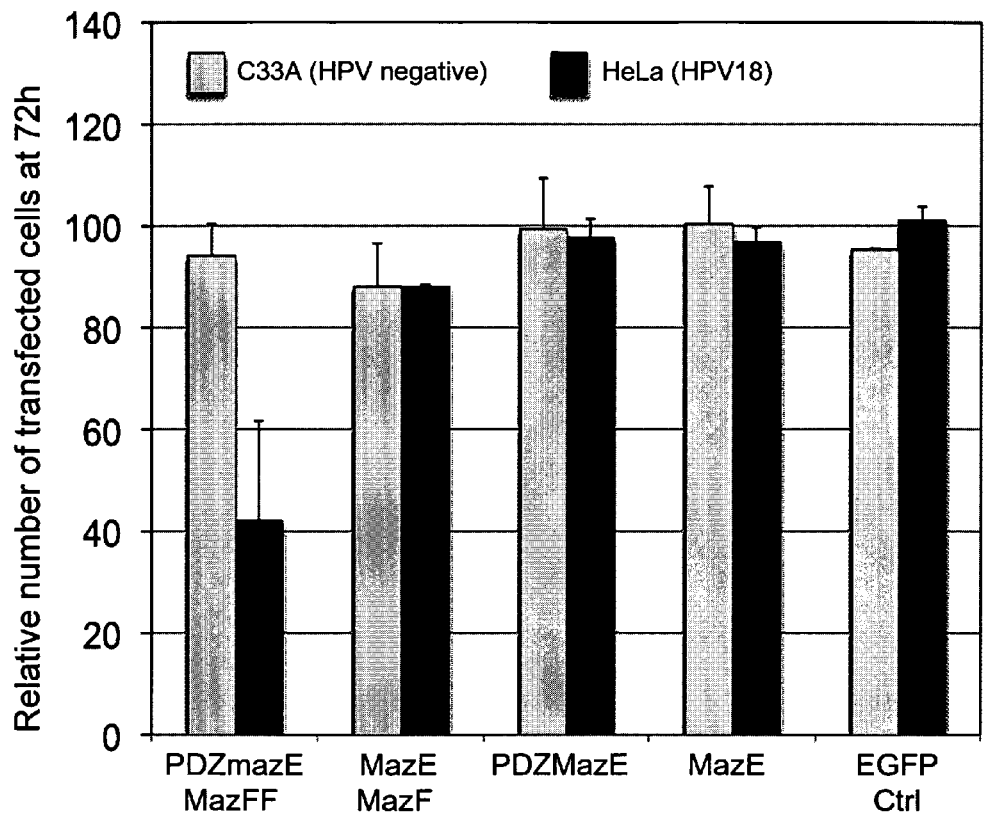

FIG. 7. PDZMazEMazF inhibits proliferation rates in HPV-positive HeLa cells, but not in control (HPV-negative) C33A cells Cervical cancer cell lines HeLa (HPV18 positive) and control cell line C33A (HPV negative) were co-transfected with a YEFP-expressing plasmid plus another plasmid expressing antitoxin MazE fused to the cs-POM used in FIGS. 4-7 and its toxic partner MazF, or wild type MazE and MazF, or PDZMazE alone, or MazE alone. Relative numbers of transfected (i.e. fluorescent) cells were measured by flow cytometry at identical time points after transfection for each sample. The analysis revealed similar numbers of transfected cells in all cases, with the single exception of HeLa cells transfected with PDZMazEMazF.

Figure 8:
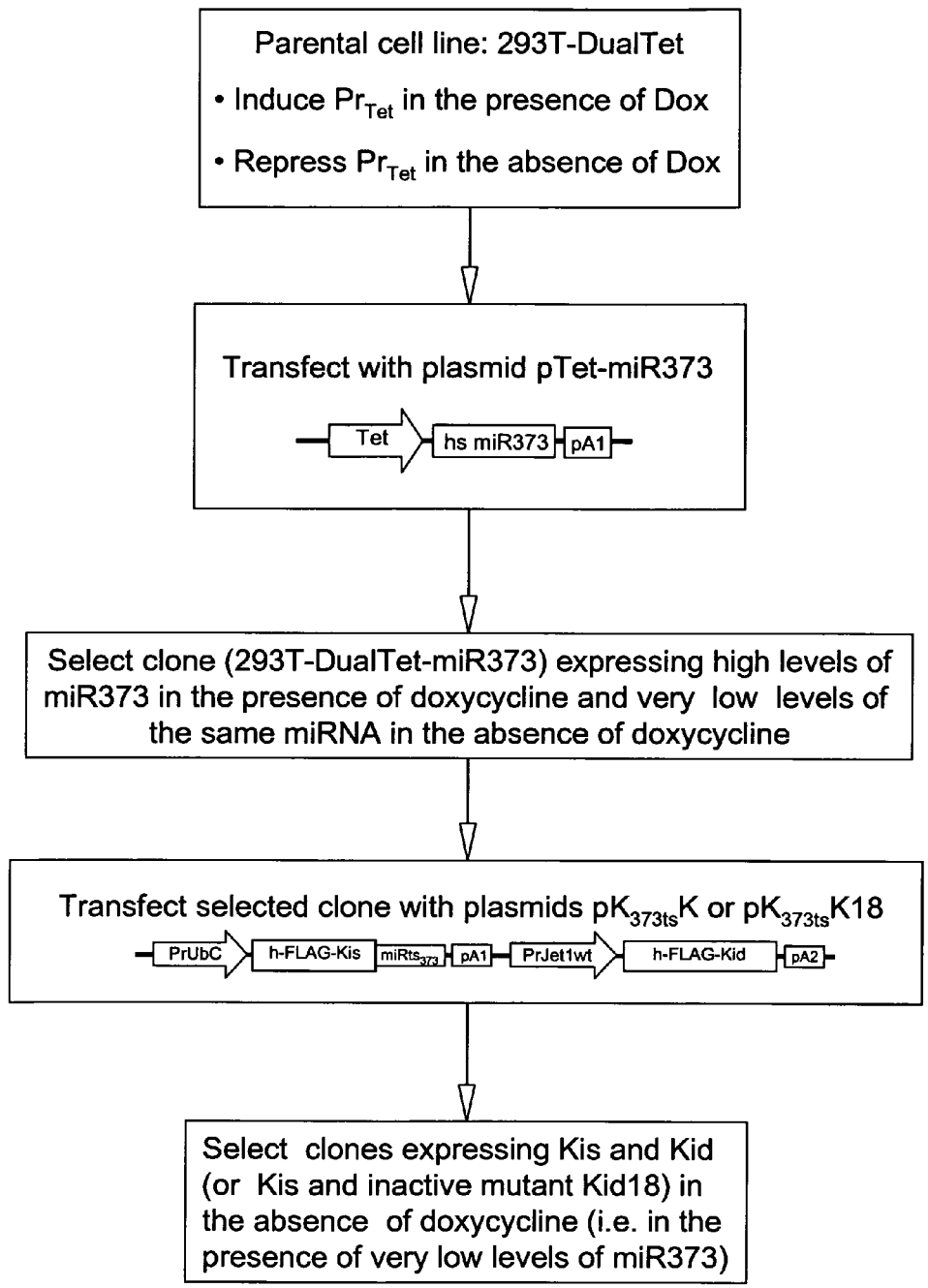

FIG. 8. Generation of a cell line to study whether miRNA target sites can be exploited as cs-POMs to modulate Kid/Kis ratios and achieve selective cell killing of cells overexpressing particular miRNA.

Expression of genes from tetracycline-responsive promoters is induced strongly by Doxycycline in 293T Dual Tet cells, but highly repressed in the absence of the antibiotic. These cells were first transfected with a plasmid carrying hsa-miR-373 under the control of a tetracycline-responsive promoter, and stable clones producing high levels of the miR-373 in the presence of doxycycline, but low in its absence, were selected. These clones were then transfected with a second plasmid carrying two independent transcriptional units: one for kid (or an inactive kid18 control mutant) and another for a kis gene followed by a sequence 100% complementary to hsa-miR-373 (pKmiR373tsK and pKmiR373Kid18, respectively). Stable clones expressing similar levels of Kid (or Kid18) and Kis in the absence of doxycycline were selected amongst these cells for further analysis.

Figure 9:
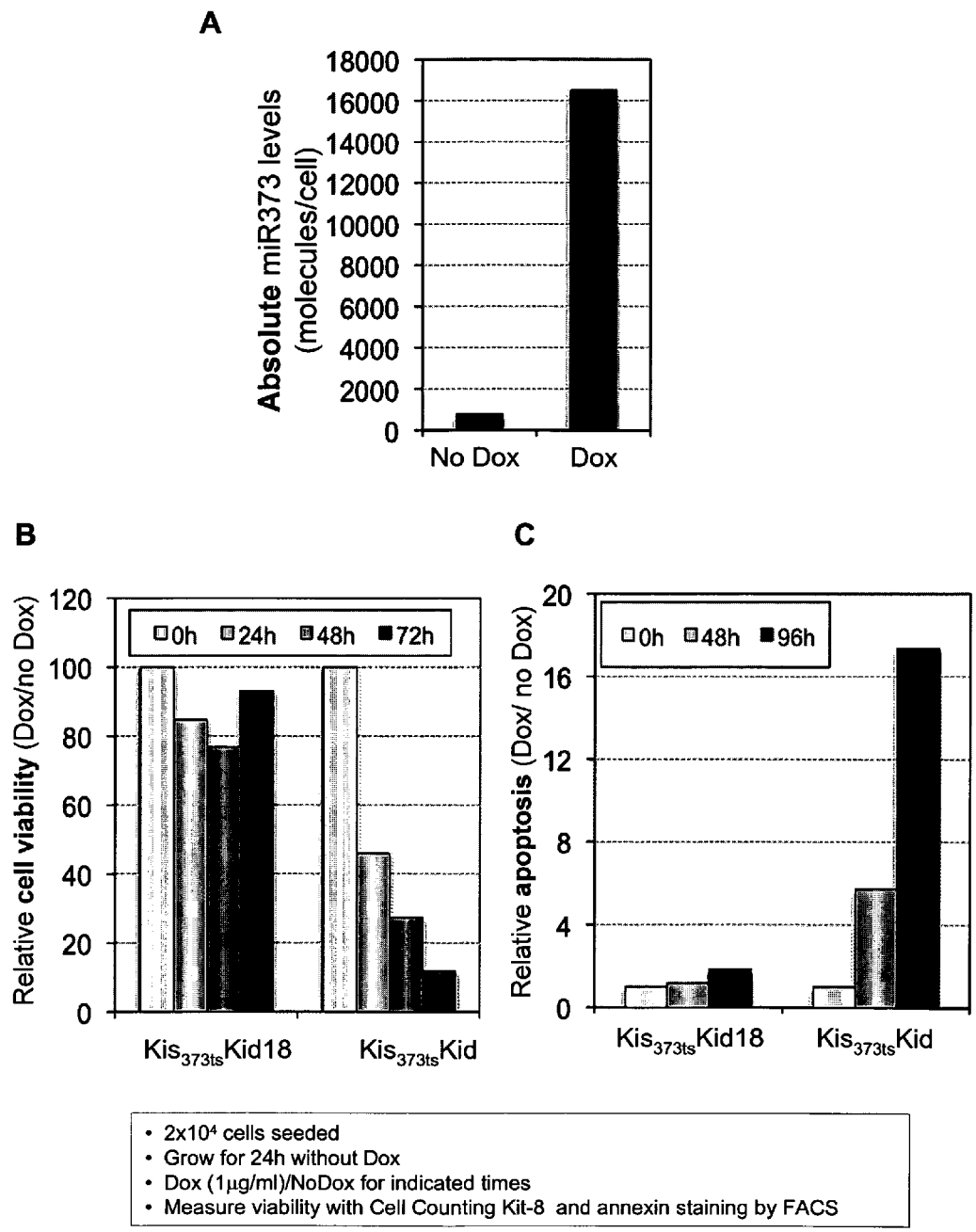

FIG. 9. Induction of miR373 expression by doxycycline reduces cell viability and increases apoptosis in cells stably transfected with pKmiR373tsK (A) Quantification of miR373 levels produced in one of the initial clones selected in FIG. 8 grown both in the absence and the presence of doxycycline. (B) Relative effect of doxycycline addition on cell viability in KmiR373K or KmiR373K18 clones derived from that shown in (A). (C) Relative effect of doxycycline addition on cell death in KmiR373K or KmiR373K18 clones derived from that shown in (A).

Figure 10:
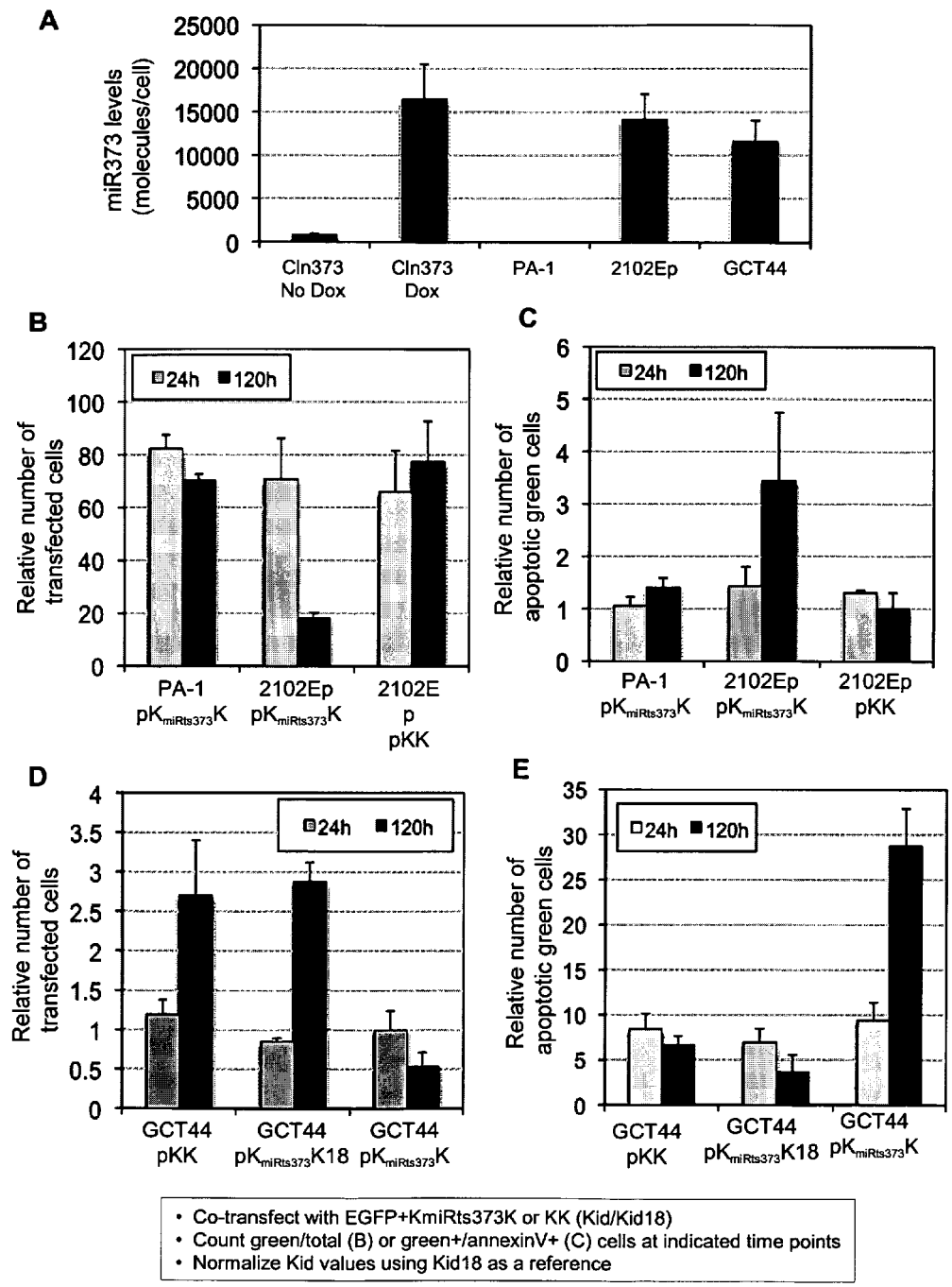

FIG. 10. Plasmid pKmiR373tsK reduces cell growth and increases cell death in human germ cell tumor cell lines that overexpress miR373.

(A) Levels of miR373 levels in human Germ Tumor cell lines PA-1, 2102Ep and GCT44 compared to those observed in the 293T Dual Tet clone analyzed in FIG. 9A. pKmiR373K (but not a derivative of this plasmid, pKK, lacking the miR373ts downstream of kis) reduces cell growth rates (B) and increases cell death (C) in germ tumor cell line 2102Ep, which expresses high levels of miR373, but not in PA-1, which is virtually devoid of this miRNA. Similarly, pKmiR373K (but not pKK or pKmiR373K18) reduces cell growth rates (B) and increases cell death (C) in germ tumor cell line 2102Ep, which also expresses high levels of miR373.

Figure 11:
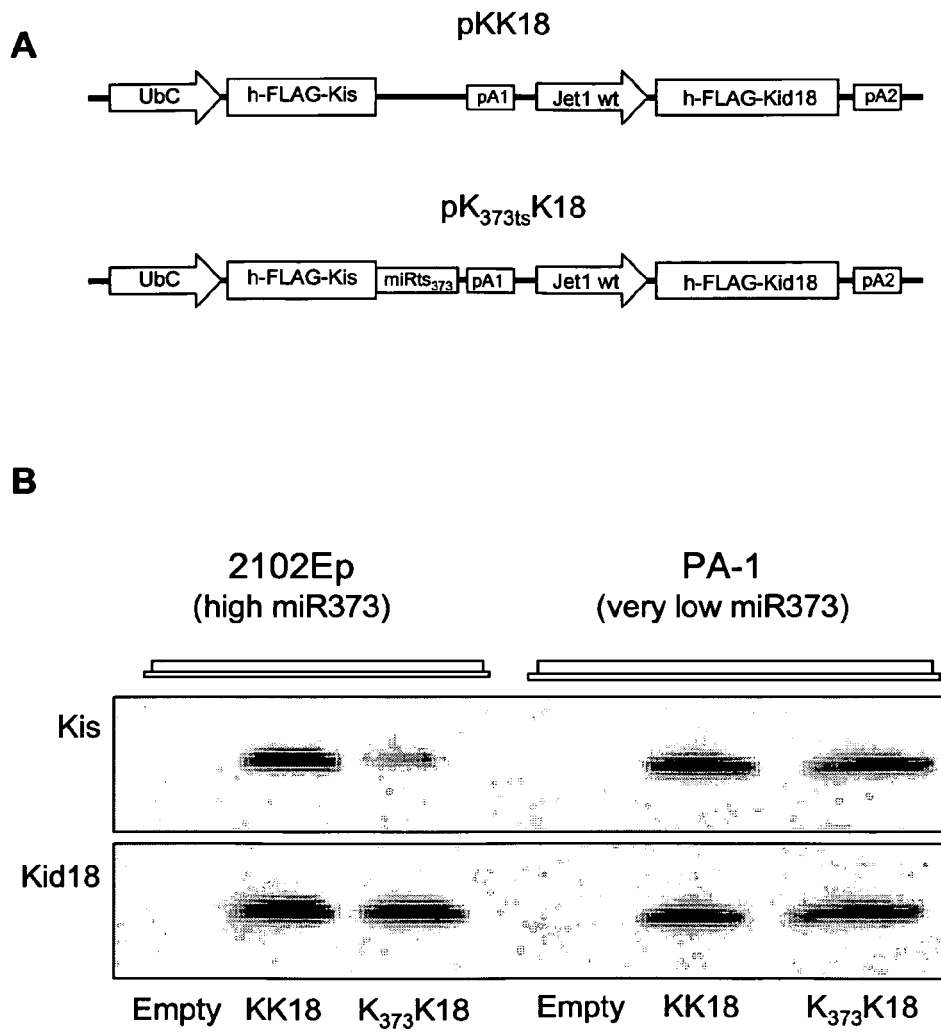

FIG. 11. The miR373ts downstream of kis in pKmiR373tsK18 increases the Kid18/Kis ratio in miR373-rich germ tumor cell line 2102Ep, compared to miR373-null control cell line PA-1.

(A) Plasmids used in the experiment (B) Western Blot analysis of the relative levels of Kis and Kid18 in 2102Ep and PA-1 cells 48 h after transfection with plasmids pKK18 or pKmiR373K18 shown in (A).

Figure 12:
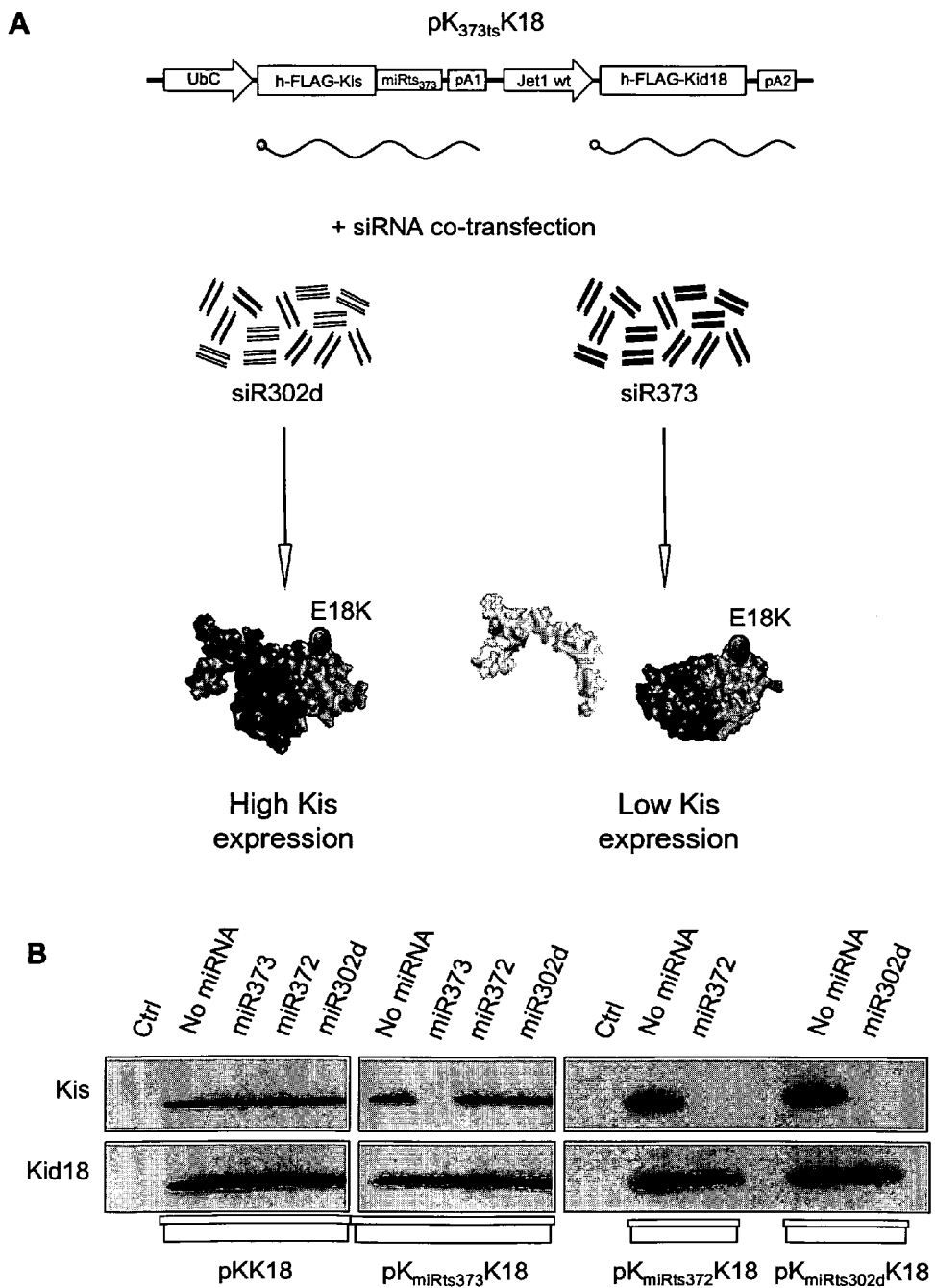

FIG. 12. The Kid/Kis ratio in cells transfected with pKmiR373tsK18 is modulated by miR373, but not by other closely related miRNAs.

(A) 293T cells were co-transfected with plasmid pKmiR373tsK18 (or control plasmid pKK18) plus either miR373, or closely related miR372 or miR502d, and the relative expression levels of Kid18 and Kis in these samples was analyzed afterwards by Western Blot. (B). Kid18/Kis ratios are not modified by miR373, miR372 or miR502d in cells transfected with pKK18 plasmid (left panels) and only miR373 increases this ratio in cells transfected with pKmiR373tsK18 (middle panels). This selectivity is not due an inability of miR372 or miR502d to function appropriately, as they increase Kid18/Kis ratios in cells transfected with control plasmids pKmiR372K18 and pKmiR502dK18, respectively (right panels) Selectivity is achieved because the miRts is cloned immediately downstream of the Kis target gene . . . .

Figure 13:
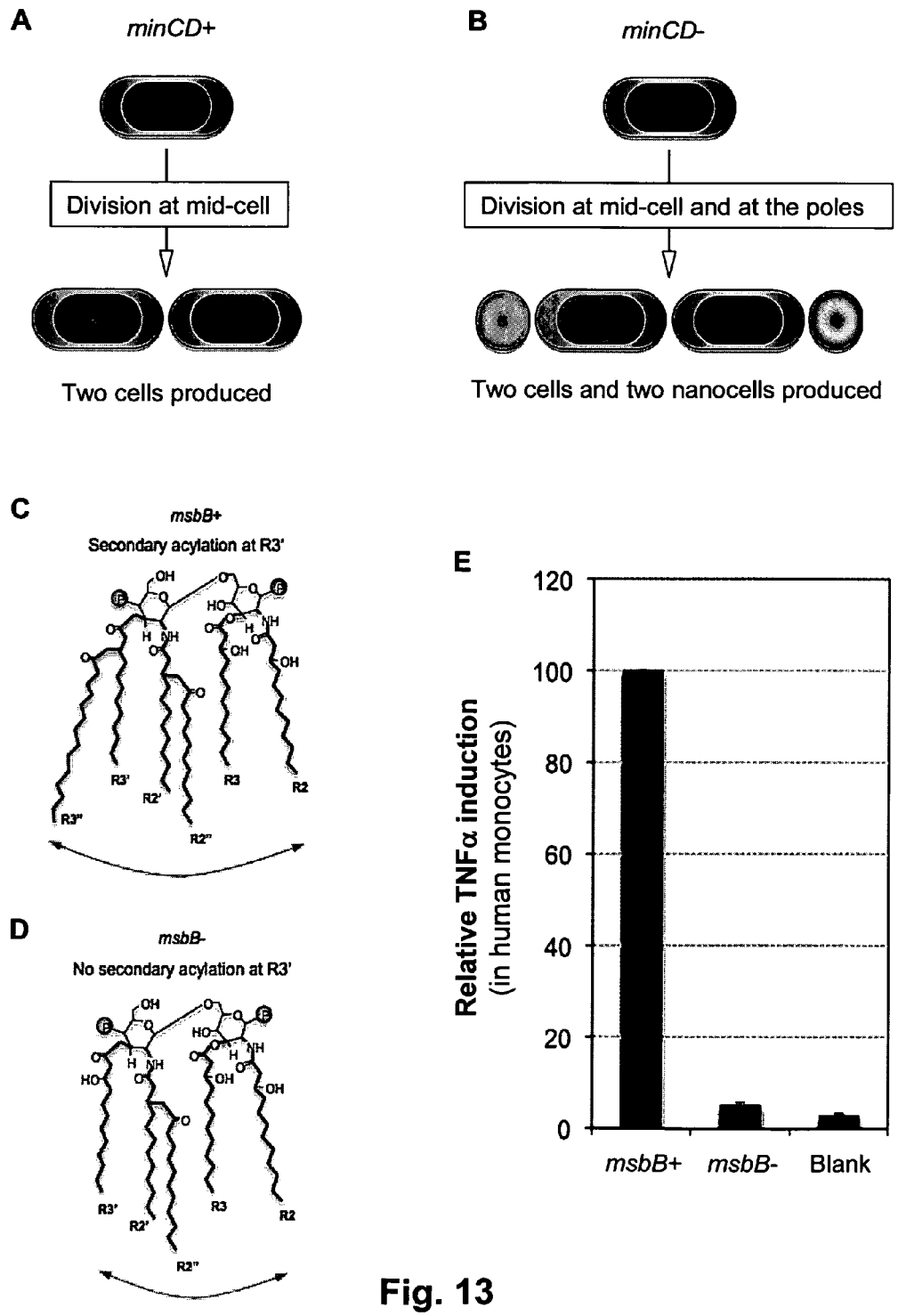

FIG. 13. Construction of an E. coli strain producing nanocells devoid of immunostimulatory LipidA.

Wild type E. coli cells divide at mid-cell to generate two identical daughter cells each cell cycle (A). Deletion of highly conserved genes minC and minD in E. coli cells produces a strain that divide at mid-cell and also at the poles, simultaneously, each cell cycle. This produces two identical, fully viable, daughter cells and two inert vesicles of 100-400 nm diameter, devoid of chromosomal DNA (nanocells). (B) Further deletion of the gene msbB in the strain describe in (A) results in a strain that produces nanocells and lacks LipidA (a potent immunostimulator of cytokine production in mammals; C) in its membrane lipopolysaccharyde layer. Instead, this strain and its derived nanocells produce a penta-acylated precursor of LipidA (D) with a highly attenuated ability to stimulate cytokine production in human cells, as shown by measuring TNFalpha induction in human monocytes (E).

Figure 14:
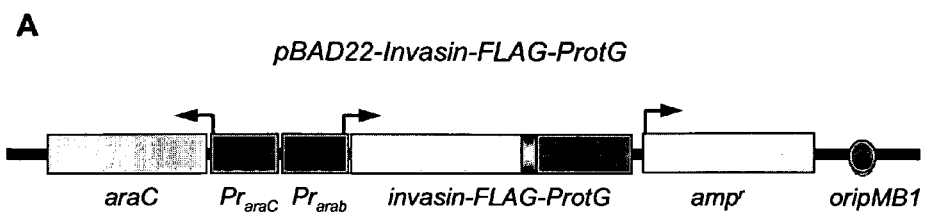
Figure 14:
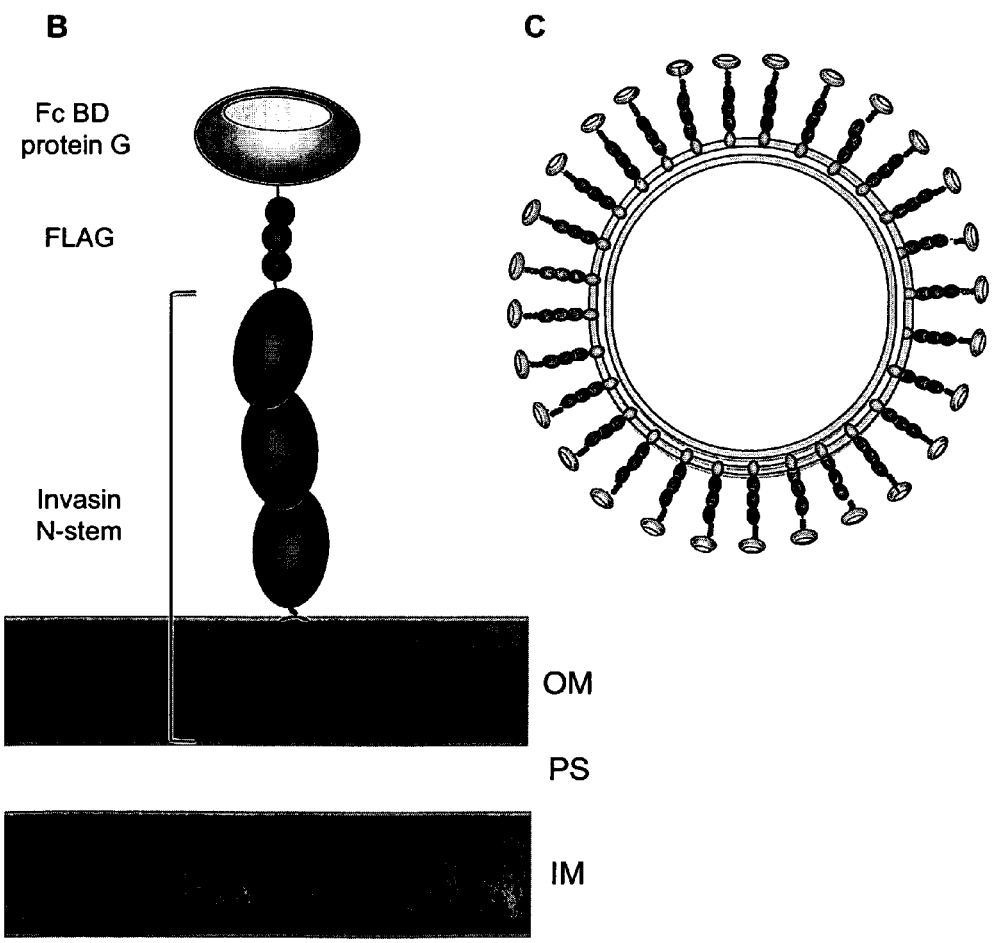

FIG. 14. In vivo production of nanocells coated with a fusion protein exposing an IgG-Fc binding domain on its external surface (A) Scheme of plasmid pBAD22-Invasin-FLAG-ProteinG. In this vector expression of a fusion gene composed (from N- to C-terminus) of residues 1-796 of the invasin protein of Yersinia pseudotuberculosis, a 3×FLAG epitope and residues 191 to 384 of the streptococcal protein G (which comprises its IgG-Fc binding domains B1, B2 and B3) can be induced by arabinose in E. coli cells. (B) Upon induction with arabinose, the invasin-3FLAG-ProtG fusion protein is produced in E. coli cells and anchors to its outer membrane. These cells and the nanocells that they produce expose a long invasin stem domain capped by the IgG-Fc binding domain of protein G (C).

Figure 15:
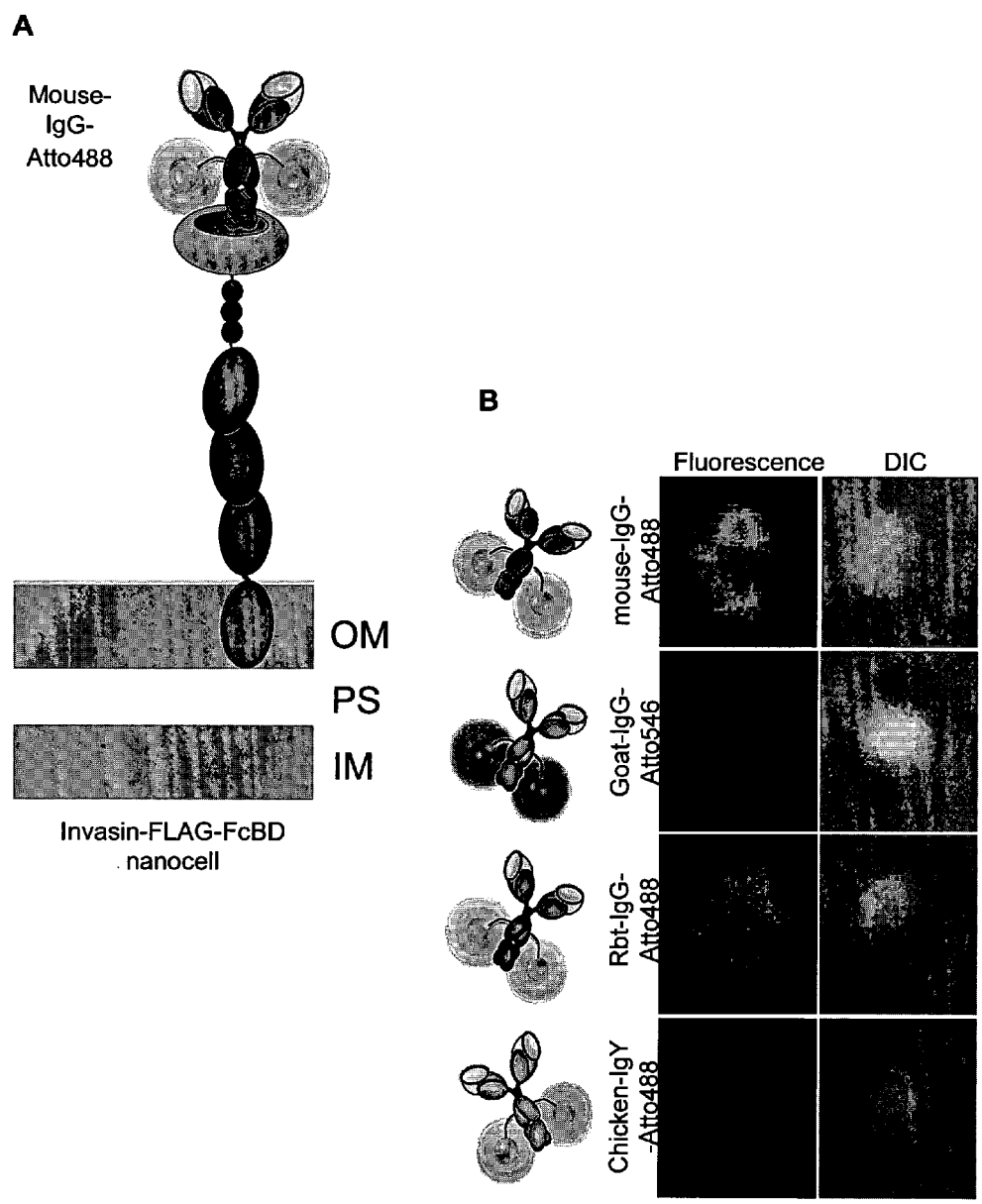

FIG. 15. Nanocells exposing multiple copies of the Fc-binding domain of protein G to the external medium can be coated in vitro with IgGs from different species.

(A) Scheme depicting the binding of an IgG, through its Fc domain, to the invasin-3FLAG-ProtG fusion protein exposed on the external surface of nanocells produced as indicated in FIG. 14. (B) DIC and fluorescent imaging of purified nanocells coated in vitro with fluorescently tagged IgGs shows that, accordingly to the Fc-binding specificity of streptococcal Protein G, rabbit, goat and mouse IgGs (but not chicken IgY) can be used to coat these nanocells.

Figure 16:
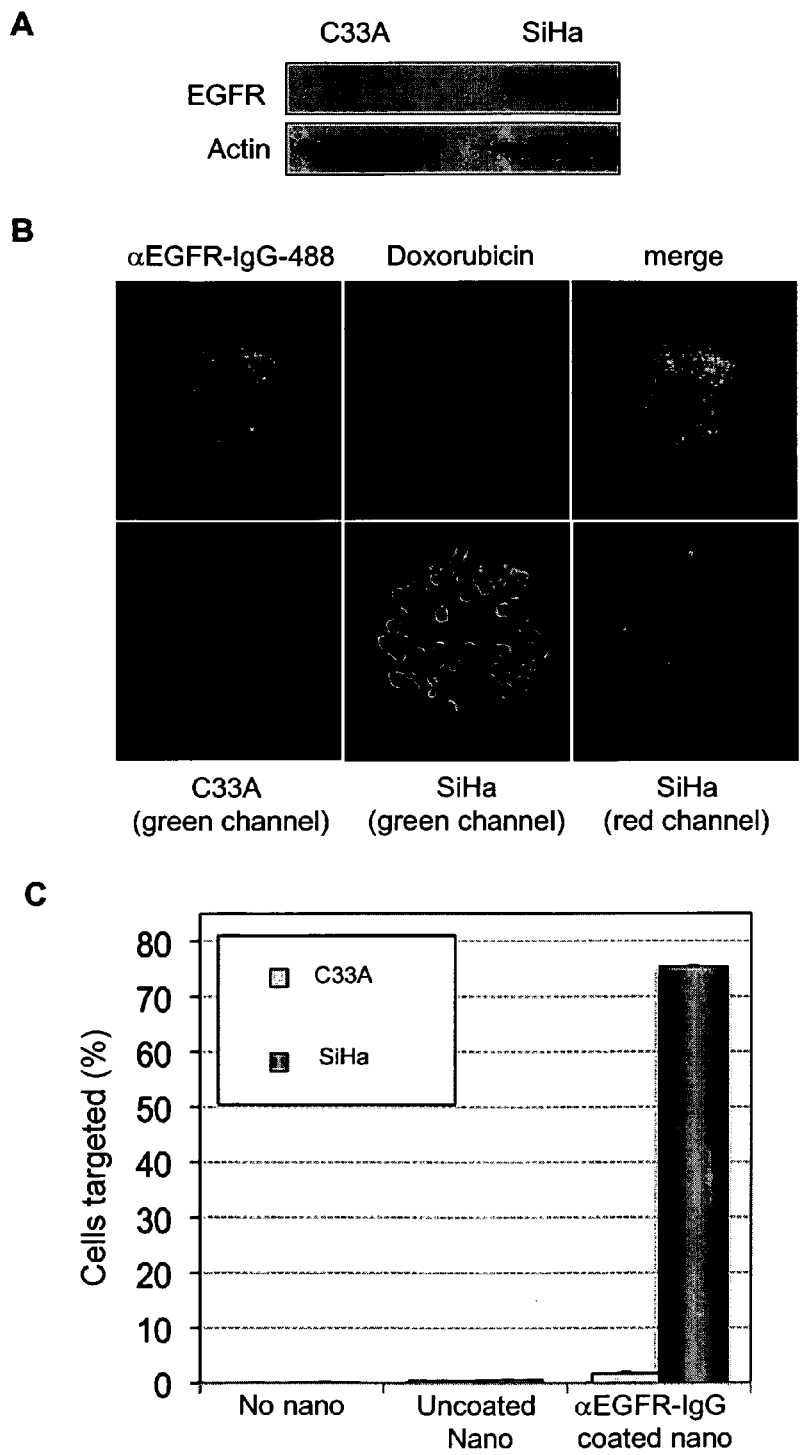

FIG. 16. Nanocells loaded with chemotherapeutic drugs and coated with specific IgGs via the invasin-FLAG-ProtG fusion protein can be directed to cells expressing the antigens recognized by such IgGs.

(A) Immunoblot of protein extracts from C33A and SiHa cells using an anti-EGFR antibody. (B) Immunofluorescent confocal images of nanocells coated with a fluorescently tagged IgG against EGFR (green channel; top left panel), their doxorubicin load (red channel; top mid panel) and merge image of both (top right panel), and of C33A cells (bottom left panel) and SiHa cells (bottom mid and right panels) incubated with those nanocells for 30 minutes. (C) Quantification by FACS show that nanocells in (B) bind a large percentage of EGFR-positive SiHa cells compared to non-coated control nanocells, but do not bind EGFR negative C33A cells.

Figure 17:
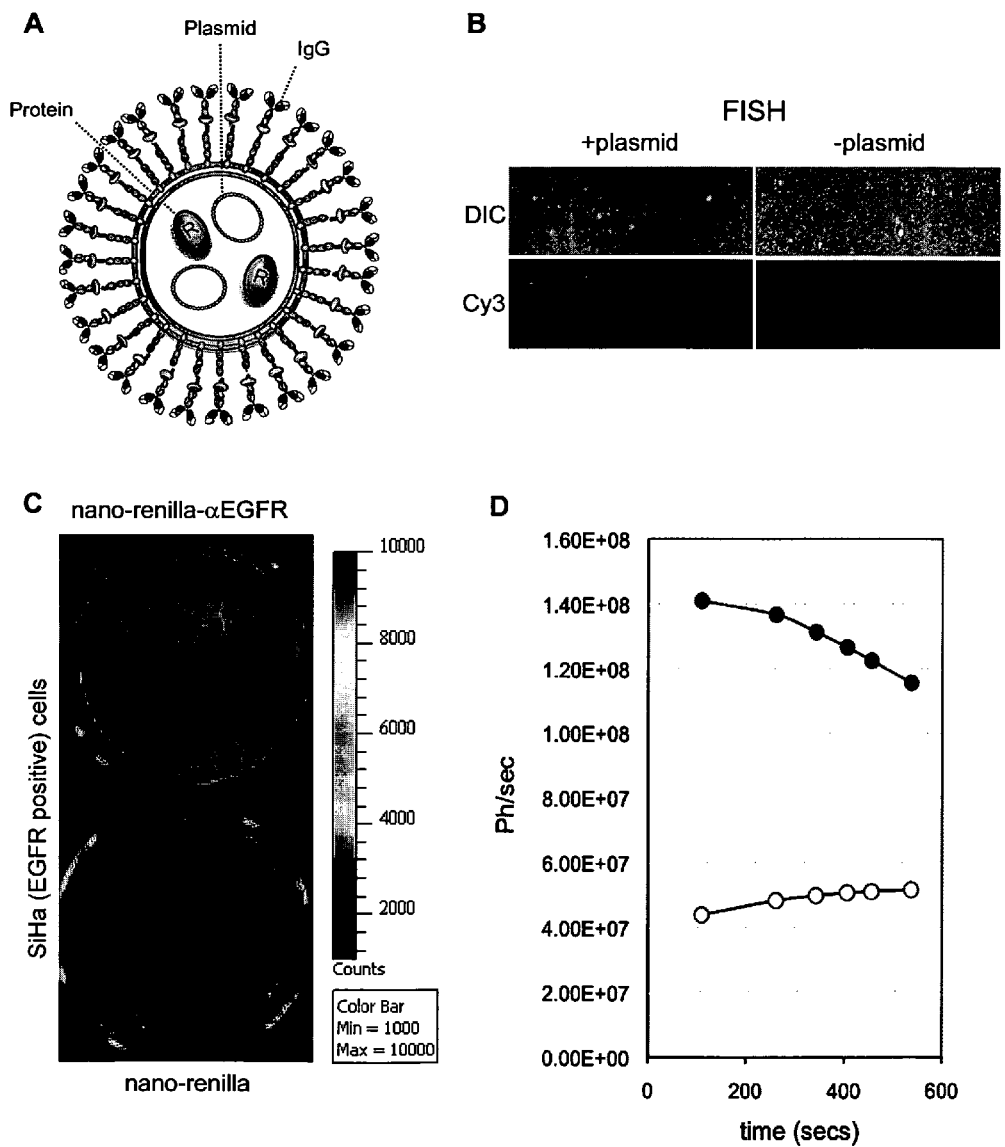

FIG. 17. Nanocells can be preloaded with plasmid DNA and proteins to deliver this type of molecules to specific human cells.

(A) Scheme depicting a nanocell coated with IgGs via the invasin-3-FLAG-ProteG anchoring protein and filled with proteins or plasmid DNAs present in parental bacterial cells during nanocell production. (B) Nanocells produced from a parental strain carrying plasmid DNA are also loaded with the same DNA, as revealed by FISH using a fluorescent DNA probe specific for such episomes. (C) Nanocells can also be preloaded with *Renilla* if the protein is expressed in parental cells during nanocell production and, when coated with an anti-EGFR IgG (top panel) these nanocells deliver the protein cargo to SiHa cells. (D) Quantification of the amount of *renilla* delivered to SiHa cells by nanocells coated (black dots) or uncoated (white dots) with an anti-EGFR IgG (C), using an IVI imaging system.

FIGS. 18 to 23 further exemplify the different aspects of the present invention using different variants of a prokaryotic toxin-antitoxin pairs operably linked to a POM, and their application in target-defined cell killing.

Figure 18:
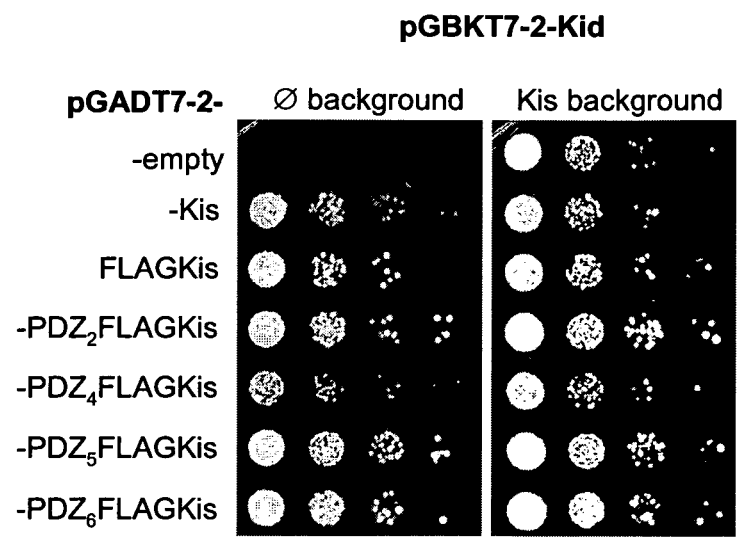

FIG. 18. The vectors pGADT7-2-FLAGKis, pGBKT7-2-E6(16), pGBKT7-2-E6(18), pGBKT7-2-Kid and pGBKT7-2-Kid18, pGADT7-2-PDZ$_2$FLAGKis (for hSCRIB$_{aa933-1126}$ fusion), pGADT7-2-PDZ$_4$FLAGKis (for hMAGI-1$_{aa293-733}$ fusion), pGADT7-2-PDZ$_5$FLAGKis (for hDIg1$_{aa221-418}$ fusion), and pGADT7-2-PDZ$_4$FLAGKis (for hDIg1$_{aa221-550}$ fusion), were used to transform AH1092 budding yeast cells carrying an additional vector from which expression of Kis (i.e. "background Kis", see below) could be induced by adding methionine to the growth media. This analysis confirmed that in the absence of background Kis proliferation of cells carrying pGBKT-7-Kid was inhibited unless pGBKT7-2-FLAGKis or any of its PDZ-Kis fusion variants was present (i.e. all PDZ-Kis variants are able to neutralize Kid toxicity).

Figure 19:
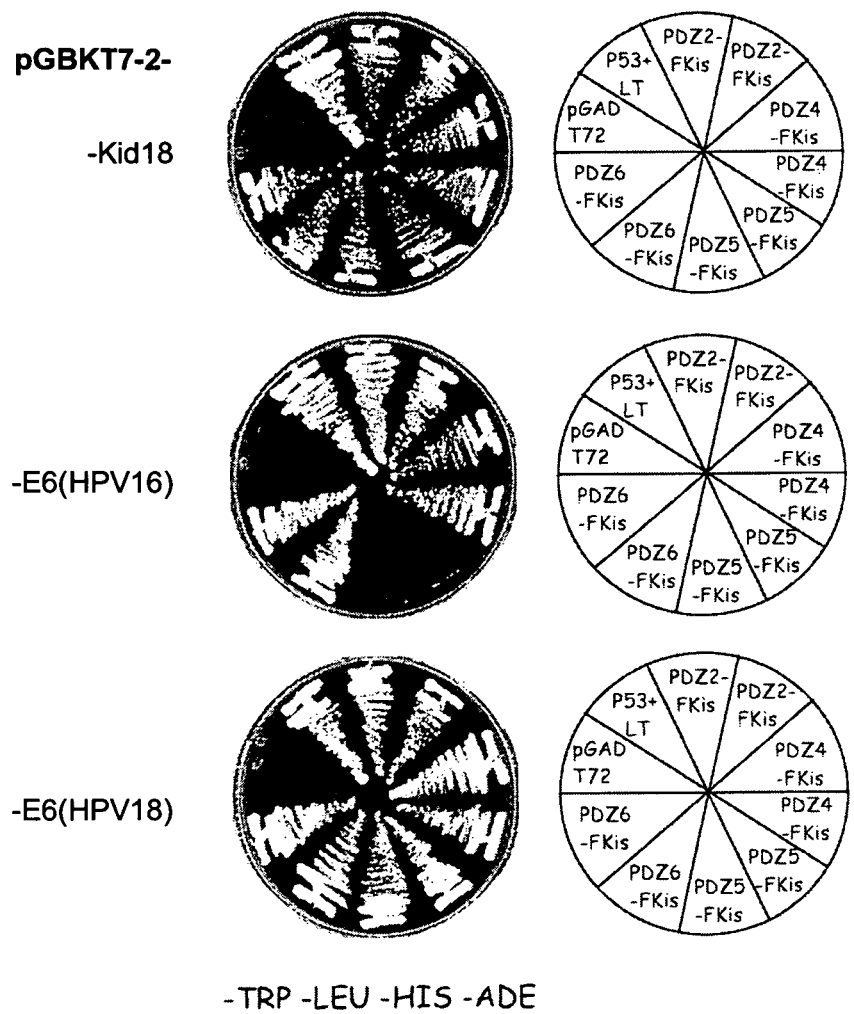

FIG. 19. Similarly, 2-Hybrid budding yeast strain SFY526 was transformed with the combinations of vectors indicated in this Figure. In this case, a pGBKT7-2-Kid18 variant, expressing an inactive Kid18 fusion protein was used, to avoid inhibition of proliferation in cells. In this assay, cell growth is dependent on the interaction between the two matchmaker fusions expressed in the cell. The analysis demonstrates that all PDZFLAGKis variants interact with Kid (Kid18) and HPV(18) E6 allowing cell growth. Interestingly, all but one (PDZ$_5$FLAGKis), interact also with HPV(16) E6. This result is in agreement with the observation that HPV 16 and HPV 18 E6 proteins bind hDgI-1 slightly differently and with different strengths, with HPV 16 E6 being consistently weaker than HPV18 E6 in its ability to interact and degrade hDgI-1 (see: Gardiol D, Kühne C, Glaunsinger B, Lee S S, Javier R, Banks L. (1999) Oncogene. 18(40):5487-96).

Figure 20:
Figure 20:
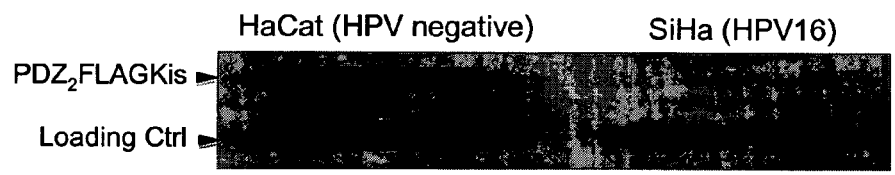

FIG. 20. pUC18CMVPDZ2FlagKisIRESKid18 pA was used to transfect HaCat (HPV-negative) and SiHa (HPV16-positive) cells. Conditions were set up to reach a 70% transfection efficiency (which was confirmed using a co-transfected EGFP-expressing plasmid). 48 h after transfection, cell extracts were prepared from these samples and analyzed by western blot using an anti-Flag antibody to determine the relative amounts of PDZFlagKis protein present in both samples. This showed that PDZ2FlagKis is abundant in HaCat cells and virtually absent in SiHa cells.

Figure 21:
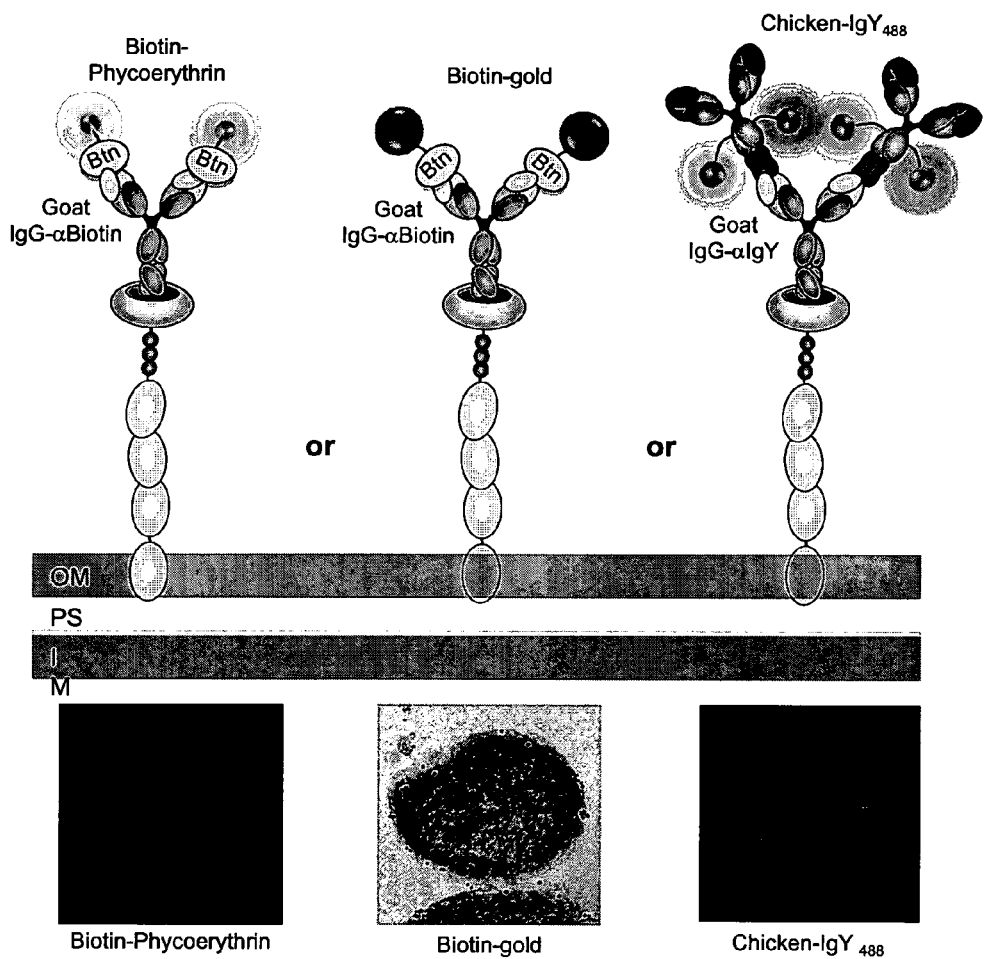

FIG. 21. Nanocells bearing the invasin-FLAG-Protein G fusion were produced as described in FIG. 15 (old POM patent) from our *E. coli* strain minCD$^-$/msbB$^-$ carrying plasmid pBAD22-invasin-FLAG-ProtG, and subsequently purified. 50 to 100 ul of our final nanocell preparations were mixed separately with 30 mg/ml of the antibodies indicated in FIG. 4 new (Goat IgG-aBiotin or Goat IgG-achickenIgY, both from Sigma) and incubated on a rocking well for 1 h at 4° C. These samples were then washed by diluting them 100 fold in 0.1% BSG solution and concentrated to the starting volume in a 3 ml AMICON MILLIPORE Stirring cell with a 300 KDa cutoff membrane, to eliminate any unbound antibody. Then the samples were incubated separately with biotin conjugated to phycoerythrin, with biotin conjugated to 10 nm diameter gold-conjugated biotin (6 mg/ml) at a 4:1000 dilution, or with a Chicken-IgY conjugated to Atto$_{488}$ (30 mg/ml at a 1:10000), as indicated in FIG. 4 new. Incubations were continued for 30 min at room temperature. Samples were then processed as follows. For gold beads nanocells were washed twice in 1 ml low salt PBS and fixed in 1% glutaraldehyde for two hours at room temperature in a gyratory wheel, before washing them four more times, now with 0.1M HEPES pH 7.8. These samples were then stored at 4° C. until imaged by transmission electron microscopy (TEM). For samples incubated with biotin phycoerythrin or with Chicken-IgY conjugated to Atto$_{488}$, 5 ul of these samples were mounted on poly-L-lysine coated coverslips with Vectashield mounting medium (Vector laboratories) and visualized using a ZEISS LSM510 (microscope).

This Figure shows that antibodies coating nanocells may be used to functionalize nanocells with additional molecules of therapeutic or diagnostic interest, via specific IgG-antigen (eg. biotin) interactions. For instance, biotin (or any other specific antigen) may be linked to superparamagnetic iron oxide nanoparticles (SPION) or ultra small SPION (usSPION) and, following the approach above, used to functionalize nanocells. SPION and usSPION are attractive candidates for various medical applications such as MRI contras agents, cell separation, cell labeling, drug delivery, magnetic nanoparticle-mediated gene transfer (magnetofection), or the induction of hyperthermia in experimental cancer therapy (Gupta A K and Gupta M. (2005) Biomaterials, 26(18):3995-4021). Nanocells may therefore be used to transport these moieties in their outer membrane and target them to specific cells in vivo and in vitro, either alone or in simultaneously to encapsulated cargoes (i.e. proteins, DNAs, RNAs and/or small molecules). Similarly, biotin (or other suitable antigen) could be linked to Gadolinium or Gallium chelates (i.e. Gd-DOTA and Ga-DOTA) and nanocells coated with an IgG recognizing the antigen above may be used to transport these compounds to specific cells in vivo and in vitro. As it happens with usPIONs, Gd-DOTA has value as a contrast agent for Magnetic Resonance Imaging of target cells in vivo and in vitro, and may also be used to induce their selective elimination by thermal ablation. Similarly Gallium isotopes (Ga67 and Ga68) chelated by DOTA could be exploited in single photon emission computed tomography (SPECT), positron emission tomography (PET) scans, and gammagraphies for diagnostic/monitoring clinical purposes. Other compounds, such as fluorescent material may be used in clinical and preclinical diagnosis of a disease (eg. cancer) or to monitor a disease response to specific treatments. In general, the approach could be exploited to transport specific molecules on the surface of nanocells, which could offer additional advantages from a therapeutic and/or diagnostic-monitoring point of view.

Figure 22:
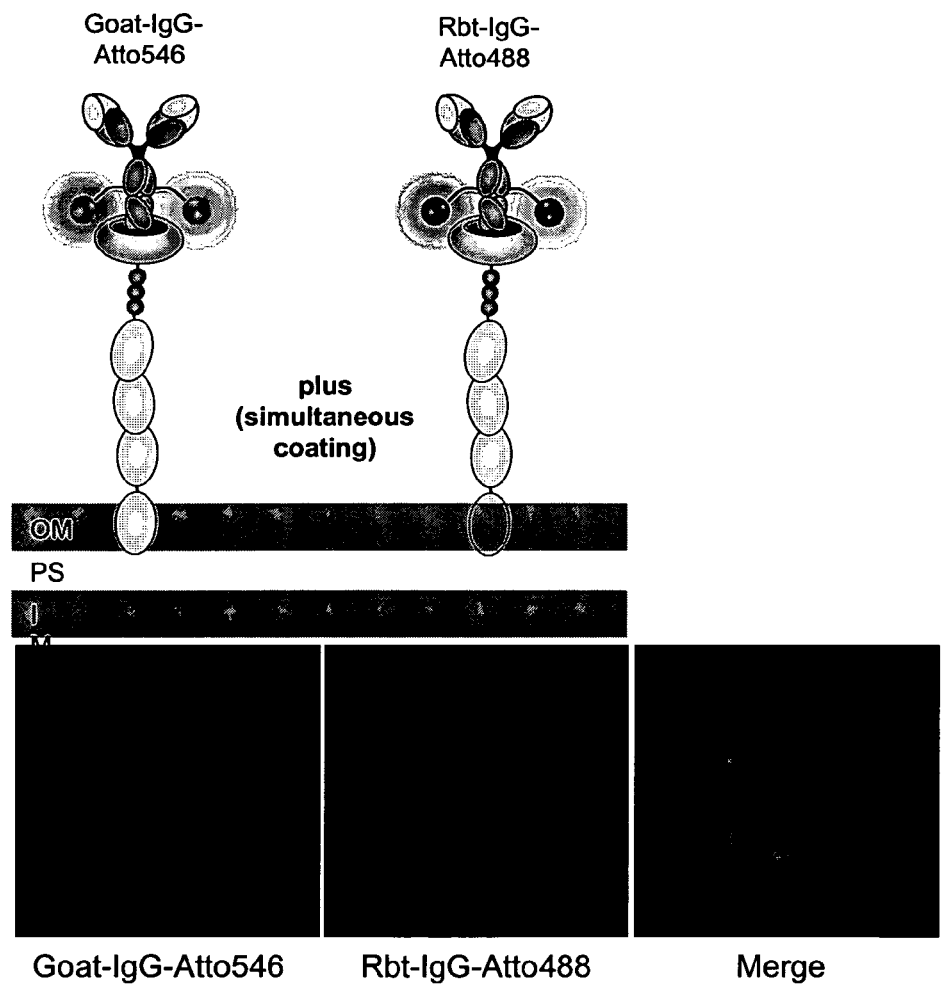

FIG. 22. Nanocells bearing the invasin-FLAG-Protein G fusion were produced as described in FIG. 15 (old POM patent) from our *E. coli* strain minCD⁻/msbB⁻ carrying plasmid pBAD22-invasin-FLAG-ProtG, and subsequently purified. 50 to 100 ul of our final nanocell preparations were mixed simultaneously with 30 mg/ml of each of the antibodies indicated in FIG. 5 new (Goat-IgG-Atto546 and Rbt-IgG-Atto488) and incubated on a rocking well for 1 h at 4° C. These samples were then washed by diluting them 100 fold in 0.1% BSG solution and concentrated to the starting volume in a 3 ml Amicon Millipore Stirring cell with a 300 KDa cutoff membrane, to eliminate any unbound antibody. 5 ul of these samples were mounted on poly-L-lysine coated coverslips with Vectashield mounting medium (Vector laboratories) and visualized using a Zeiss LSM510 microscope).

This Figure demonstrates that single nanocells can be coated with different antibodies simultaneously. This enables to use some antibodies to direct nanocells to specific cells (as shown in FIGS. 16 and 17 of old POM patent) and, at the same time, using additional antibodies to functionalize the same nanocells with other moieties of therapeutic/diagnostic interest (as discussed in the previous FIG. 4 new). Thus the strategy of producing nanocells with invasin-FLAG-Protein G inserted in their membrane and exposing the protein G tip to the exterior increases the versatility and modularity of nanocells and facilitates their use in theranostic applications.

BEST MODE FOR CARRYING OUT THE INVENTION

Material and Methods
1. Plasmids Construction
   1.1. Construction of PDZKis-IRES-Kid plasmids and variants (FIGS. 4 and 7). pUC18 was digested with HindIII and EcoRI and a new MCS containing SfiI-SpeI-BclI-BamHI-BstXI-NcoI-NheI-XhoI-NotI sites was subcloned in there using appropriate annealed oligos. The BamHI-IRES2-BstXI fragment from plasmid pIRES2-DsRed (Clontech) was then subcloned into the BamHI and BstXI sites of the plasmid above to generate pUC18IRES2. A DNA fragment SfiI-Kozak+ATG-MAGI-1$_{aa293-733}$-(Gly)$_4$-SpeI was amplified using cDNA from HeLa cells, and subcloned into pUC18IRES2 to generate pUC18PDZ4IRES. Similarly, fragments SpeI-FLAG-Kis-BamHI or SfiI-Kozak-ATG-FLAG-Kis-BamHI were obtained by PCR using appropriate oligos, and these were cloned into SpeI-BamHI or SfiI-BamHI sites of pUC18IPDZ4RES2, respectively, to generate pUC18FlagKisIRES and pUC18PDZ4FlagKisIRES. DNA fragments BstXI-Kid-XhoI and BstXI-Kid18-XhoI were amplified from mR1wt and mR118 by PCR (Pimentel et al., 2005) and cloned into the same sites of pUC18FlagKisIRES and pUC18PDZ4FlagKisIRES to make plasmids pUC18 FlagKisIRESKid, pUC18FlagKisIRESKid18, pUC18PDZ4FlagKisIRESKid and pUC18PDZ4FlagKisIRESKid18. A small synthetic polyadenylation signal was produced by annealing appropriate oligos, which were then cloned between XhoI and NotI sites into the four plasmids described above. Finally, a HindIII-CMV-SfiI fragment was amplified by PCR from plasmid pIRES2-DsRed and subcloned between the same sites in the plasmid containing the synthetic polyA. This generated the pUC18FlagKisIRESKidpA set of plasmids shown in FIG. 4A. To produce the MazE/MazF variants of these vectors (used in FIG. 7), NsiI-MazE-BclI and BstXI-MazF-XhoI fragments were amplified by PCR from *E. coli* genomic DNA and cloned sequentially into their flanking sites in pUC18FlagKisIRESKidpA and pUC18PDZ4FlagKisIRESKidpA to produce pUC18FlagMazEIRESMazFpA and pUC18PDZ4FlagMazEIRESMazFpA. MazF was eliminated from the latter to plasmids (to make MazE-only controls) by digestion with BstXI and XhoI and re-ligation. Subsequently, the SfiI-NotI fragment from the resulting four plasmids were subcloned into the same sites in pUC18CMVPDZ4FlagKisIRESKidpA to produce its PDZ4FlagMazE-IRES-MazF, PDZ4FlagMazE-IRES, Flag-MazE-IRES-MazF and FlagMazE-IRES counterparts, used in FIG. 7.

1.2. Construction of E6-IRES-YEFP plasmids and variants (FIG. 4). Using appropriate annealed oligos restriction sites SpeI-BstXI-NcoI were inserted between KpnI and BamHI sites of vector pUHD 10.3 Hygro (Gossen and Bujard) to generate plasmid pUHD MCS. A BstXI-EYFP-BamHI fragment was produced by PCR from pEYFP-N1 (Clontech) and cloned between the BstXI and BamHI sites of pUHD MCS to form plasmid pUHD EYFP. The SpeI-IRES-BstXI from pUC18IRES2 sequence was subcloned into the same sites of pUHD EYFP to form plasmid pUHD IRES EYFP. A fragment KpnI-E6-SpeI was made by PCR using cDNA produced from CaSki (HPV16E6) and HeLa (HPV18E6) cells as template, and these fragments were cloned into the KpnI and SpeI sites of pUHD IRES EYFP to make pUHD E6(16) IRES EYFP and pUHD E6(18) IRES EYFP depicted in FIG. 4.

1.3. Construction of pTRE-miR373 plasmid and of pKmiR373tsK variants (FIGS. 8-11). A fragment comprising the genomic hsa-miR373 precursor was obtained digesting plasmid miRVec373 (Voorhoeve, le Sage et al. 2006) with KpnI and BamHI, and this fragment was cloned into the same sites of the tetracycline regulatable vector pUHD10.3Hygro (Gossen and Bujard), to create pTRE-miR373 (FIG. 8). A transcriptional unit formed by human-codon optimized FlagKis with a Kozak consensus sequence around the start codon and flanked upstream and downstream by human Ubiquitin-C promoter and a BGH polyA signal sequence was cloned in a pUC derivative plasmid. miRNA target sites 100% complementary to hsa-miR373, hsa-miR372 or hsa-miR502d were cloned immediately downstream of the kis stop codon in these contructs, using appropriate single restriction sites. Similarly, transcription units bearing human-codon optimized FlagKid or Flag-Kid18 with a consensus Kozak sequence around the start codon and flanked upstream and downstream by human a synthetic JeT promoter (Tornoe, Kusk et al. 2002) and a SV40 polyA signal sequence were synthetically produced and cloned in similar pUC derivative plasmid. Kis and kid (or kid18) transcription units were assembled in tandem in a single vector as shown in FIG. 7, using a pUC18 derivative carrying an additional transcriptional unit encoding the blasticidin resistance cassette from a PGK promoter, to allow selection of stably transfected clones if the construct was genomically integrated.

1.4. Construction of plasmid pBAD22-Invasin-3FLAG-ProtG and pBAD22-invasin-3FLAG-ProtG/R8Luc (FIGS. 13 and 17). A DNA fragment comprising the coding sequences for the first 796 residues of the *Y. pseudotuberculosis* invasin gene and flanked by NheI and SfoI sites was produced synthetically. Similarly, a second DNA fragment comprising SfoI-(Gly)$_5$-3×FLAG-(Gly)$_5$-Streptococcal ProtG$_{aa191-384}$-stopcodon-SacI-XbaI-HindIII was also produced synthetically. These DNA fragments were digested with NheI-SfoI and SfoI-HindIII, respectively, and subcloned in a tripartite ligation in pBAD22 (Guzman reference) digested with NheI and HindIII, to produce the plasmid shown in FIG. 13. pBAD22-Invasin-FLAG-ProtG-RLuc8 is a variant of the latter plasmid. It expresses an stable and hiperactive mutant of *Renilla* Luciferase (RLuc8; Loening et al., 2006), Loening, A. M., Fenn, T. D., Wu, A. M. & Gambhir, S. S. Consensus guided mutagenesis of *Renilla* luciferase yields enhanced stability and light output. Protein Eng Des Sel 19, 391-400 (2006) in the same operon as Invasin-FLAG-ProtG. To make this plasmid an RLuc8 gene preceded by its on Shine Dalgarno sequence and flanked by XbaI and HindIII sites was synthetically generated and cloned between these same sites in the pBAD22-Invasin-FLAG-ProtG plasmid.

2. Construction of Human Cell Lines and Bacterial Strains.

2.1. Construction of clones 293TDualTet-miR373-KmiRts373K and 293TDualTet-miR373-KmiRts373K18 (FIGS. 8 and 9). Cell line 293TRSID Dual-Tet (Tetracycline) (Ausserlechner, Obexer et al. 2006) was transfected with pTRE-miR-373 and stable clones were selected with 100 µg/ml hygromycin, in the absence of doxyxycline. Clones wee selected that showed high expression levels of miR373 in the presence of doxycycline, and very low in its absence (FIG. 8 and below). These clones were then transfected with either pKmiR373tsK or pKmiR373tsK18 and stable clones were selected (in the absence of doxycline) using 5 µg/ml blasticidine. Suitable clones, producing detectable levels of Kid (or Kid18) and Kis in the absence of doxycycline, were selected for further analysis by western blot.

2.2. Construction of *E. coli* strains producing nanocells. To make the basic nanocell producing bacteria, genes minC and minD were disrupted by homologous recombination in strains DHB4 and LMG194, as instructed by Datsenko and Wanner, 2000. The msbB gene was subsequently disrupted on these strains, following the same protocol, to generate a strain that not only produces nanocells but also lacks immunostimulatory LipidA in its membrane. All antibiotic resistance genes used to disrupt minCD and msbB genes were flanked by FRT sites allowing us to remove them from the genome of the resulting strains using FLP recombinase, again as instructed by Datsenko and Wanner, 2000.

3. Generation of Data According to Figures

FIG. 4. HEK293 cells were transiently transfected at ~50% confluency with all 1:1 combinations possible between the Kis/Kid plasmids and the YEFP plasmids shown inf FIG. 4A. Transfections were carried out using Qiagen Effectene, according to manufacturer's instructions and using both plasmids in a ratio of 3 copies of Kis/Kid plasmid per copy of EYFP plasmid. Cells were incubated overnight and the growth medium was changed the next day. Cells were imaged 48 h after transfection using a Canon G2 camera connected to a Zeiss Axiovert 40 microscope with a UV light source. An EGFP filterset was used to view EYFP. The base of each well was marked to allow several consistent fields to be monitored over time.

FIG. 5. HPV-positive HeLa (90% confluency) and SiHa (50%) cells and HPV-negative C33A (50%) control cells were co-transfected with the Kis/Kid plasmids shown in FIG. 4A and a GFP-expressing plasmid, at a 9:1 ratio, using Lipofectamine 2000 (Invitrogene) and following manufacture's recommendations. In order to determine the proportion of apoptotic cells in a population, cells were stained with Cy5-conjugated Annexin-V (Source BioScience Autogen) and analyzed by flow cytometry. At the times indicated in the Figure, samples were harvested by gentle trypsinisation and resuspended in 500 µl Annexin-V binding buffer (Source BioScience Autogen) and incubated at room temperature in the dark for 5 minutes. Finally, cells were passed through a 70 µm strainer (BD) to remove any clumps and then analyzed immediately in a BD LSR II flow cytometer. Cells were initially gated by EGFP pulse area into green and non-green populations, with the gate being set by reference to non-transfected controls. Annexin-V staining was then analyzed separately for both populations by considering Cy5 pulse area. Statistics were generated according to the percentage of Annexin-V positive cells in the green and non-green populations of each sample. 50,000 cells were analyzed per sample. All experiments were repeated at least three times.

FIG. 6. HEK293 cells were transiently co-transfected with plasmids pUC18PDZ4FlagKisIRES and either pUHD-IRES-EYFP (no E6) or pUHD-E6(16)-IRES-EYFP (E6HPV16) using Qiagen Effectene and following the manufacturer's instructions. A 1:3 ratio of E6 or empty plasmid to PDZ-Kis plasmid was used. Eight hours after transfection, cells were trypsinised and the homogeneous cell suspension was distributed equally between the wells of a 6-well plate and returned to the incubator for another 16 h. At this point (24 h postransfection), the first ($t_o$) sample was collected by detaching cells with a cell scraper and pelleting them at room temperature by centrifugation at 1,000 g for 5 min. This cell pellet was washed with 1 ml PBS and centrifuge in a 1.5 ml Eppendorf tube and, after removing the supernatant, stored at −80° C. until further analysis. Growth medium in the remaining wells was aspirated and replaced with prewarmed medium containing 40 µg/ml cycloheximide (Sigma) and plates were returned to the incubator. From this point onwards one well per sample was processed as before until the end of the experiment. Protein extracts from this samples were analyzed by western blot using anti-Flag (to detect PDZFlagKis) and anti-EGFP (to detect YEFP) antibodies.

FIG. 7 HPV-positive HeLa (60% confluency) and HPV-negative C33A (50% confluency) control cells were co-transfected with the MazE/MazF plasmids and a GFP-expressing plasmid, at a 9:1 ratio, using Lipofectamine 2000 (Invitrogene) and following manufacture's recommendations. At the times indicated in the Figure, samples were harvested by gentle trypsinisation and fixed in 2% formaldehyde for 10 minutes at room temperature. Finally, cells were washed in PBS and then analyzed in a BD LSR II flow cytometer. Cells were gated by EGFP pulse area into green and non-green populations with the gate being set by reference to non-transfected controls. Statistics were generated according to the percentage of the green and non-green populations of each sample. 50,000 cells were analyzed per sample. All experiments were repeated at least three times.

FIG. 8. To quantify levels of miR-373 in selected clones, these were grown in the presence and absence of doxycycline (1 mg/ml) for 24 hours before harvesting them (in triplicate) for qRT-PCR analysis of miR373. Cells were counted before harvesting using a haemocytometer in order to determine the approximate number of cells per reaction and consequently microRNAs per cell. microRNA extraction was carried out using Ambion miRVana Kit, and extracts were diluted to 5 ng/µl and then subjected to qRT-PCR (in triplicate) using the Ambion microRNA Assay Kit. To measure absolute expression levels of miR373 per cell, a standard curve was generated by a dilution series of known copy number of a miR-373 RNA oligonucleotide, identical to the cellular miR-373 and subjected to identical qRT-PCR procedures. From this standard curve the absolute number of miR-373 molecules per reaction could be extrapolated. The copy number per cell could then be FIG. 9. To analyze relative viability of our clones after induction of miR373 expression, 293TDualTet-miR373-KmiRts373K and 293TDualTet-miR373-KmiRts373K18 cells were seeded at a low density (2×10^4 cells/well) in a 24 well plate. 24 hours after seeding they were induced with 1 μg/ml doxycycline and assayed with a viability reagent (Cell Counting Kit-8, Dojindo) over a 5-day time-course, following manufacture's instructions. For this, the number of metabolically active cells present in each sample was determined measuring the absorbance at 450 nm of 2 μl of media on a nanodrop, 4 hour after incubation with the viability reagent. To analyze relative cell death in the same samples, Annexin-V staining was used to determine the proportion of apoptotic cells within a population. Cells were stained with Cy5-conjugated Annexin-V (Source BioScience Autogen) following the manufacturer's protocol. In brief, after harvesting 1 well of a 6 well plate by trypsinization and centrifugation 3000 rpm for 5 minutes, the cell pellet was resuspended in 250 μl Annexin binding buffer. 2.5 μl Cy5-Annexin-V was added to the samples, which were incubated for 5 minutes in the dark to stain. Cells were filtered through a 70 μm cell strainer and analyzed by flow cytometry. Gating parameters were established with reference to a positive control population for Annexin-V positivity treated with 10 nM staurosporin (Sigma) overnight. All experiments were repeated at least three times.

FIG. 10. Quantification of miR-373 levels in germ cell tumor cell lines PA-1, 2102Ep and GCT44 was carried out as specified previously for 293TDualTet-miR373 clones. To analyze the effect of plasmis pKmiR373tsK and its variants on their relative cell growth and cell death rates, these cells were nucleofected at a ratio of 10 molecules of the KisKid plasmid per molecule of a EGFP reporter plasmid. GCT cells were nucleofected using the Lonza Amaxa Nucleofector I device. Buffers, Nucleofector programme and conditions were optimised using the Lonza Nucleofector Optimization Kit, and following manufactures's instructions. Cells were monitored for as long as possible after transfection given their relative growth rates and the initial seeding density required to avoid toxicity. At different times after transfection samples were trypsinized gently and pelleted at 3000 rpm for 5 minutes. The resulting pellet was resuspended in an appropriate volume of PBS and passed through a 70 μm cell strainer before analyzing them by FACS in a BD LSR II flow cytometer. Forward and side scatter parameters were adjusted to exclude debris. Gating for EGFP established green and non-green populations by reference to transfected and non-transfected controls. Rate of apoptosis was quantified as described for 293TDualTet-miR373 clones. 50,000 events were analyzed per sample and each experiment was repeated at least three times.

FIG. 11. To confirm whether a correlation exists between cell death or cell protection observed in the GCT cell lines and miR-373 dependant Kis regulation, relative levels of Kis and Kid18 proteins were analyzed in 2102Ep and PA-1 cell lines grown in the presence (1 μg/ml) and absence of Doxycycline. Cells were transfected as indicated above with the Kis Kid18 constructs, both with and without a miR-373TS downstream of Kis, and samples were harvested 48 hours later. Protein extracts from these samples and untransfected cells were analyzed by western blot using specific antibodies against Kid and Kis.

FIG. 12. 293T cells were co-transfected with pKmiR373tsK18, pKmiR372tsK18, pKmiR502dtsK18 or pKK18constructs and the siRNAs 373, 372, or 502d, as indicated in the figure, and the extent of Kis and Kid18 expression was analyzed 24 hours after transfection by Western Blot. DNAs and RNAi were co-transfected into 293T cells using Lipofectamine 2000 (Invitrogen). Cells were seeded in a 6 well plate 24 hours pre-transfection such that they were 90% confluent at the time of transfection. 0.5 μg DNA and 10 pmol (10 nM final concentration) of RNAi were diluted in 250 μl OptiMEM. In a separate tube 6 μl Lipofectamine2000 was diluted in 250 μl OptiMEM. The 2 suspensions were incubated for 5 minutes at room temperature and then mixed. The DNA and Lipofectamine2000 mixture was incubated for 20 minutes at room temperature during which time the culture medium of the cells was replaced with 500 μl OptiMEM. The DNA:lipid complexes were then added dropwise to the cells and incubated for 6 hours. After this time the transfection complexes were aspirated from the cells and 2 ml fresh growth medium was applied. After 24 hours cells were harvested and protein extracts analyzed using antiKis and antiKid antibodies.

FIG. 13. Isolation and quantification of Lypopolysaccharide and quantificacion of its effect on TNFα release by human monocytes. LPS was extracted from bacterial cells using a LPS Extraction kit (iNtRON Biotechnology) according to the manufacturer's protocol. To determine the concentration of LPS in the samples, purpald dye colorimetric assay (Lee & Tsai, 1999), which measures the oxidized un-substituted terminal vicinal glycol groups (UVTG) in 2-keto-3-deoxyoctonate (Kdo) and L-(or D-)glycero-D-manno-heptose of LPS molecules. Purified KDO (Sigma) was used as a standard. and the concentration of LPS was expressed as the millimolar concentration, considering there are four molecules of KDO per LPS molecule. This concentration was converted to milligrams. To quantify the attenuation of LPS extracted from our modified bacterial strains compared to wiltdype LPS, induction of TNF-α release in Human Peripheral Blood Mononuclear Cells (HPBMC; TCS CellWorks) exposed to LPS extracted from these strains was used. For this HPBMC cells were grown in 24-well plates (2.5×10$^5$ cell/well) and incubated 24 hours with 2.5 μg LPS isolated from our wildtype and msbB-null bacterial strains. To measure the amount of TNFα released by cells after 24 this time the growth media collected for each sample, passed through a 20 μm filter, and analyzed by an ELISA kit (ebioscience), according to the manufacturer's protocol.

FIG. 15. Production and purification of nanocells from strain minCD$^-$/msbB$^-$ and carrying plasmid pBAD22-Invasin-FLAG-ProtG. To produce nanocells, 10 fresh colonies of our minCD$^-$ msbB$^-$ E. coli cells, transformed with plasmid pBAD22Invasin-FLAG-ProtG were used to inoculate 100 ml of LB medium, plus ampicillin (100 μg/ml). This culture was grown at 30° C. at 230 rpm shaking overnight. With this culture, a new one was started at an OD600 nm of 0.05 in 500 ml of ZY medium supplemented with ampicillin (100 μg/ml), 2 mM MgSO$_4$, 50 mM Na$_2$HPO$_4$, 50 mM KH$_2$PO$_4$, 25 mM (NH$_4$)$_2$SO$_4$, 0.2× trace metals mixture (Studier, 2005), and 0.05% arabinose. This culture was grown for 2 h at 30° C. and 230 rpm shaking, to induce production of the invasin-FLAG-ProtG fusion protein in parental cells. These cells were collected by centrifugation at 2000 g for 10 min at room temperature, and resuspended in 10 ml of the same growth medium. This cell suspension was used to inoculate 3 L of the same medium at an OD600 nm of 0.05, which was grown at 30° C., 230 rpm for two hours, before adding 0.05% arabinose again and repeat growth in the same conditions for another two hours. At this point, nanocells were purified from the culture. To do this, the culture was centrifuged at 2000 g for 10 min at room temperature, and the pellet (mostly parental cells) was discarded. The supernatant of the step above was centrifuged at 8200 g for 13 min at 4° C., and the resulting pellet was resuspended in 12 ml (final volume) of Phosphate-buffered saline containing 0.1% cold water fish skin gelatine (BGS, Sigma). This mixture was stirred gently for 15 minutes at room temperature. 4 ml of this suspension was gently poured on top of clear Beckma Coulter gradient tubes containing a discontinuous gradient constituted of the following layers of optiprep solution (Sigma) diluted in PBS (from bottom to top): 2.5 ml of 40%, 5 ml of 30%, 10 ml of 20%, 5 ml of 10% and 2.5 ml of 6%. These tubes were then centrifuged at 10000 rpm, 7 min and 4° C. in a SW 28 Ti Beckman rotor, and all content of each tube from the middle of the 30% optiprep solution upwards was collected using a syringe with a 21 gauge needle. This mixture was diluted up to 200 ml in 0.1% BSG, and concentrated down to 12 ml in a Stirred cell (AMICON Millipore) with a 300 kDa pore membrane. This concentrated sample was transferred to a glass beaker and stirred again for ~10-15 min at room temperature. This sample was subjected to the same optiprep gradient as before, but this time centrifuging the tubes at 10000 rpm for 5 min at 4° C. After this second centrifugation gradient, a dense band should be observed around the intersection between the 30% and the 20% Optiprep layers. This band, and all the solution above it, was collected from each tube using a syringe with a 21 gauge needle, pooled together, and diluted and concentrated again as before, using the stirred cell with a 300 KDa cut off. The concentrated solution resulting from this step was applied to a third centrifugation gradient as before, once more at 10000 rpm for 5 min at 4° C. In this case only a faint band should be observed around the bottom half of the 20% optiprep layer. This band, and all the solution above it, was collected, and washed and concentrated down to 6-8 ml, as before. This sample is constituted mainly by pure nanocells but it also contains parental bacterial cells in very low numbers. To kill these the sample was diluted 10 times in LB and grown for 2 h at 30° C. in a shacking incubator and 230 rpm before growing them for another two hours in the same conditions but in the presence of 250 µg/ml of Kanamycin and 50 µg/ml of chloramphenicol. This culture was then diluted with 250 ml of 0.1% BSG and concentrated down to 5 ml in a stirred cell with a 300 KDa cut off membrane, as before. These washing and concentrating steps were repeated four times, letting the final concentration step to reduce the volume of the sample down to 500 µl, which could be kept at 4° C. for a few days or at −80° C. in 10% trehalose in PBS for long-term storage. 50-100 ml of our nanocell preparations were mixed separately with 30 mg/ml of the fluorophore-conjugated antibodies indicated in the figure (all of them from Sigma) and incubated in a rocking wheel for 1 hr at 4° C. This sample was diluted 100 fold in 0.1% BSG solution and concentrated to the starting volume in a 3 ml Amicon Millipore stirred cell with a 300 KDa cutoff membrane, to eliminate the unbound antibody. 5 µl of these samples were mounted in Poly-L Lysine coated coverslips with Vectashield mounting medium (Vector Laboratories) and visualized using a Zeiss LSM510 confocal microscope.

FIG. 16. Nanocells were produced and purified as indicated above, but they were incubated with 250 µg/ml Doxorubicin for 12 h in a rocking wheel at room temperature before the step in which kanamycin and chloramphenicol are used to kill any parental cell contaminating the preparation of nanocells. Once pure, nanocells were incubated 1 h at 4° C. with 60 µg/ml of a goat α-human EGFR IgG (Sigma) previously conjugated to Atto-488 using a Lightning Link Conjugation kit (Innova Biosciences) following manufacturer's recommendations. Excess antibody was washed as described above. $1 \times 10^6$ SiHa (EGFR-positive) or C33A (EGFR-negative) cells were plated in agarose-coated wells to keep them in suspension, rocking them very gently inside a tissue culture incubator for 1 h before adding 100 µl of our doxorubicine-loaded nanocells coated with α-EGFR IgG-Atto 488 and incubating them in the same conditions for another 3 hr. After this, 5 µl of cells were processed for microscopy as indicated before and analyzed in a Zeiss LSM510 confocal microscope (FIG. 16B). The remaining sample was analyzed by flow cytometry in a BD LSRII Flow cytometer system (BD Biosciences) (FIG. 17C).

FIG. 17. Nanocells were produced from $minCD^-$ $msbB^-$ E coli cells carrying either a pUC derived plasmid (FIG. 17B) or the bicistronic expression plasmid pBAD22-Invasin-FLAG-ProtG/Rluc8 (FIGS. 18C and 18D), and purified as indicated before. For FIG. 17B, Fluorescence-in situ Hybridization (FISH) was carried out. The same pUC derived plasmid present in parental cells was used as a probe to detect plasmid DNA in nanocells. A purified sample (1 µl of that plasmid was linearized with restriction endonuclease and recovered from a 1% agarose gel before labeling it with Biotin 16-dUTP (Roche) using a random-primed DNA labeling kit (Abott Molecular Inc.), following manufacturer's recommendations. Once labeled, the plasmid was resuspended in hybridization buffer containing 50% formamide (Sigma), 10% dextran sulphate (sigma), 2×SSC, 40 mM sodium phosphate buffer, 1×Denhardt's solution (Sigma), 10 µg of competitor bacteria genomic DNA and 10 µg of salmon sperm DNA (Sigma). This plasmid probe was denatured at 80° C. for 2 min and placed at 37° C. prior to use. Nanocells produced from bacterial cells carrying the pUC derivative were fixed by adding equal volume of fixation solution (methanol:acetic acid [3:1]) and incubated for 5 min at room temperature. Then, 10 µl of the fixed cell sample was spread on a poly-L-lysine-coated glass slide and allowed to dry at room temperature. The sample on the slide was denatured in prewarmed denaturing solution (70% formamide, 2×SSC) at 75° C. for 2 min and immediately snap-cooled in ice-cold 70% ethanol, and dried for 5 min before transferring it into a series of ethanol baths (70%, 90%, and absolute) for 5 min each, and dried again. Freshly prepared Lysozome (25 mM Tris-HCl, 10 mM EDTA, 50 mM glucose, 2 mg/ml lysozyme [pH 8.0]) was spread onto the sample and the slide was kept at room temperature for 10 min. The slide was washed in 2×SSC for 5 min and dehydrated through an ethanol series (70%, 90%, and absolute, for 5 min each) and air-dried. The plasmid DNA probe was then added directly to the nanocells on the slide, overlaid with a coverslip and finally sealed with Cow-Gum, before incubating them for 16 h in a humidified chamber at 42° C. Then, the slides were washed twice in wash buffer (50% formamide, 1×SSC) at 45° C. for 5 min, followed by two further washes in 0.1×SSC at 45° C. for 5 min. Slides were incubated in a solution containing 4×SSC, 0.05% Tween-20 (Sigma)) for 3 min and removed. To prevent nonspecific binding of the detection reagents, sample was blocked by incubating with 100 µl of 4×SSC, 3% bovine serum albumin (Sigma) at 37° C. for 20 min. The slide was washed in 4×SSC, 0.05% Tween-20 to remove excess blocking agent. For probe detection, a three-layer immunofluorescent detection reaction was used. Firstly the slide was incubated for 40 min at 37° C. with Avidin-Cy3 diluted 1:400 in a solution containing 4×SSC, 0.1% Tween 20, and 1% BSA. Excess detection reagent was removed by washing with three times with 4×SSC, 0.1% Tween 20, followed by amplification with a Biotin anti-Avidin conjugated secondary antibody at a dilution of 1/300 for 30 min. After that, the slides were washed 3 times with 4×SSC, 0.1% Tween 20 and incubated with Avidin-Cy3 diluted (1:400) for 40 min. Slides were mounted with vectashield mountant (VectaShield containing; Vector) and analyzed with an Axiolmager M2 fluorescence microscope (Zeiss) equipped with filter sets for Cy3, FITC and Cy5. For FIGS. 18C and 18D, $1\times10^6$ SiHa cells were seeded in 6 well tissue culture wells 24 hr before experiment. Both αEGFR-coated and -uncoated samples of our nanocell produced from a parental strain carrying the bicistronic plasmid pBAD22invasin-FLAG-ProtG/RLuc8 were added to our cultured cells, and incubated with them for 3 hr at room temperature in a rocking platform. Non-bound nanocells were removed by thorough triplicate washes with PBS, before adding fresh media with luciferine. Luciferase content in these nanocells and their binding to our cultured SiHa cells was quantified on an In vivo imaging system (IVIS200 Caliper; LifeSiences). Light output was measured as photons/sec/cm2/steridian).

Construction of Two-Hybrid Vectors for the Analysis of the Interaction and Neutralization of the Toxin Kid by Different PDZ-Kis Variants.

Sense and antisense oligonucleotides containing NdeI-SfiI-EcoRI were annealed to each other, and the resulting dsDNA was inserted between NdeI and EcoRI of plasmids pGADT7 and pGBKT7 (Matchmaker system, Clontech), to generate pGADT7-2 and pGBKT7-2, respectively. DNA encompassing SfiI-SpeI-FLAGKis-BamHI, SfiI-SpeI-Kid-EcoRI, SfiI-SpeI-Kid18-EcoRI, SfiI-SpeI-HR-HPV(16) E6-PstI and SfiI-SpeI-HR-HPV(18) E6-PstI were obtained by PCR using appropriate oligonucleotides and DNA templates. The latter DNA fragments were subcloned between SfiI and BamHI (SfiI-SpeI-FLAGKis-BamHI) of pGADT7-2, between SfiI and PstI (SfiI-SpeI-HR-HPV(16) E6-PstI and SfiI-SpeI-HR-HPV(18) E6-PstI) of pGBKT7-2 or between SfiI-EcoRI of pGBKT7-2 (SfiI-SpeI-Kid-EcoRI and SfiI-SpeI-Kid18-EcoRI), to generate pGADT7-2-FLAGKis, pGBKT7-2-E6(16), pGBKT7-2-E6(18), pGBKT7-2-Kid and pGBKT7-2-Kid18, respectively.

Similarly, DNA fragments SfiI-Kozak+ATG-hSCRIB$_{aa933-1126}$-(Gly)$_4$-SpeI, SfiI-Kozak+ATG-hMAGI-1$_{aa293-733}$-(Gly)$_4$-SpeI, SfiI-Kozak+ATG-hDlg1$_{aa221-418}$-(Gly)$_4$-SpeI, and SfiI-Kozak+ATG-hDlg1$_{aa221-550}$-(Gly)$_4$-SpeI were amplified using cDNA from HeLa cells, and subcloned between NdeI-SpeI sites of vector pGABT7-2-FLAGKis, to generate 2hybrid vectors pGADT7-2-PDZ$_2$FLAGKis (for hSCRIB$_{aa933-1126}$ fusion), pGADT7-2-PDZ$_4$FLAGKis (for hMAGI-1$_{aa293-733}$ fusion), pGADT7-2-PDZ$_5$FLAGKis (for hDlg1$_{aa221-418}$ fusion), and pGADT7-2-PDZ$_4$FLAGKis (for hDlg1$_{aa221-550}$ fusion), respectively.

Construction of pUC18CMVPDZ2FlagKisIRESKid18 pA Variant and Analysis of PDZ2Kis Abundance in HaCat (HPV-Negative) and SiHa (HPV16-Positive) Cells Transfected with that Vector.

pUC18CMVPDZ2FlagKisIRESKid18 pA was made as described previously for pUC18CMVPDZ4FlagKisIRESKid18 pA but using the PCR product SfiI-Kozak+ATG-hSCRIB$_{aa933-1126}$-(Gly)$_4$-SpeI instead of SfiI-Kozak+ATG-hMAGI-1$_{aa293-733}$-(Gly)$_4$-SpeI.

The invention claimed is:

1. A biological system for diminishing cell growth or inducing selective killing of target cells comprising a vehicle with a first nucleic acid sequence or amino acid sequence encoding for a prokaryotic toxin of a prokaryotic toxin-antitoxin pair, and a second nucleic acid sequence or amino acid sequence encoding for the corresponding prokaryotic antitoxin of the prokaryotic toxin-antitoxin pair, characterized in that the toxin and/or the antitoxin is operably linked to a protein output modifier (POM) that comprises a nucleic acid sequence or amino acid sequence that modifies the relative rate of transcription, mRNA stability, mRNA translatability or protein stability of the toxin and/or antitoxin thereby changing the relative ratio in the concentration of the toxin and/or the antitoxin within the target cells and/or, where applicable, within non-target cells by decreasing the antitoxin outputs in the target cells relative to the toxin outputs, and/or decreasing the toxin outputs in the non-target cells relative to the antitoxin outputs.

2. The system according to claim 1, wherein the protein output modifier (POM) is selected from the group consisting of promoter/operator sequence(s), miRNA target site(s), 3'-UTRs or ubiquitin ligase target domain(s).

3. The system according to claim 1, wherein the protein output modifier (POM) contains one or more target sequences for a cellular POM interacting molecule that is (over)expressed in the target cells and/or, if applicable, in non-target cells, and that interacts with the one or more target sequences of the POM, thereby resulting in a decrease of the toxin outputs in the non-target cells and/or decrease of the antitoxin outputs in the target cells.

4. The system according to claim 3, wherein the protein output modifier (POM) contains one or more PDZ domains from HR-HPV-E6 target cellular proteins and wherein the cellular POM interacting molecule is the E6 oncogene from High Risk HPV serotypes that interacts with said PDZ domain(s).

5. The system according to claim 2, wherein the protein output modifier (POM) is a miRNA target site and the cellular POM interacting molecule is a miRNA that interacts with said miRNA target site.

6. The system according to claim 5, wherein the miRNA target site is 100% complementary to the miRNA that targets it and wherein the miRNA target site is positioned immediately downstream of the target gene.

7. The system according to claim 1, wherein the protein output modifier (POM) is a 3'-UTR sequence in the toxin or antitoxin nucleic acid sequence.

8. The system according to claim 1, wherein the protein output modifier (POM) contains a promoter/operator sequence that decreases the rate of transcription of the antitoxin in the target cells, and/or decreases the rate of transcription of the toxin in the non-target cells.

9. The system according to claim 1, wherein the toxin-antitoxin pair is selected from the group consisting of kid/kis, CcdB/CcdA, MazF/MazE, ChpBK/ChpBI, RelE/RelB, ParE/ParD, HipA/HipB, PhD/Doc, Hok/Sok, YafM/YoeB, YafN/YafO, YgjM/YgjN, YgiT/YgiU, DinJ/YafQ, VapB/VapC, HipB/HipA, HicB/HicA, and their homologs in other organisms.

10. The system according to claim 1, wherein the protein output modifier (POM), the prokaryotic toxin and the prokaryotic antitoxin are contained in a single or in independent carrier plasmids or viruses, wherein the toxin and antitoxin are transcribed from the same single promoter or from independent promoters.

11. A pharmacological composition, comprising a vehicle with a first nucleic acid sequence or amino acid sequence encoding for a prokaryotic toxin of a prokaryotic toxin-antitoxin pair, and a second nucleic acid sequence or amino acid sequence encoding for the corresponding prokaryotic antitoxin of the prokaryotic toxin-antitoxin pair, wherein the toxin and/or the antitoxin is operably linked to a protein output modifier (POM) that comprises a nucleic acid sequence or amino acid sequence that modifies the relative rate of transcription, mRNA stability, mRNA translatability or protein stability of the toxin and/or antitoxin thereby changing the relative ratio in the concentration of the toxin and/or the antitoxin within the target cells and/or, where applicable, within non-target cells by decreasing the antitoxin outputs in the target cells relative to the toxin outputs and/or decreasing the toxin outputs in the non-target cells relative to the antitoxin outputs, and a pharmaceutical carrier.

12. A biological system, comprising a vehicle with a first nucleic acid sequence or amino acid sequence encoding for a prokaryotic toxin of a prokaryotic toxin-antitoxin pair, and a second nucleic acid sequence or amino acid sequence encoding for the corresponding prokaryotic antitoxin of the prokaryotic toxin-antitoxin pair, wherein the toxin and/or the antitoxin is operably linked to a protein output modifier (POM) that comprises a nucleic acid sequence or amino acid sequence that modifies the relative rate of transcription, mRNA stability, mRNA translatability or protein stability of the toxin and/or antitoxin thereby changing the relative ratio in the concentration of the toxin and/or the antitoxin within the target cells and/or, where applicable, within non-target cells by decreasing the antitoxin outputs in the target cells and/or decreasing the toxin outputs in the non-target cells relative to the antitoxin outputs, for use in the treatment of a pathological bacterial or fungal disease, or cancer.

13. The system according to claim 12, wherein the vehicle is delivered to the target cells by means of nanocells (minicells).

14. A drug delivery system for delivering a vehicle to target cells, wherein the vehicle comprises a first nucleic acid sequence or amino acid sequence encoding for a prokaryotic toxin of a prokaryotic toxin-antitoxin pair, and a second nucleic acid sequence or amino acid sequence encoding for the corresponding prokaryotic antitoxin of the prokaryotic toxin-antitoxin pair, wherein the toxin and/or the antitoxin is operably linked to a protein output modifier (POM) that comprises a nucleic acid sequence or amino acid sequence that modifies the relative rate of transcription, mRNA stability, mRNA translatability or protein stability of the toxin and/or antitoxin thereby changing the relative ratio in the concentration of the toxin and/or the antitoxin within the target cells and/or, where applicable, within non-target cells by decreasing the antitoxin outputs in the target cells relative to the toxin outputs, and/or decreasing the toxin outputs in the non-target cells relative to the antitoxin outputs, wherein the drug delivery system comprises nanocells containing the vehicle, characterized in that the nanocells are coated with one or more antibodies that recognize antigens specifically expressed by said target cells by exposing multiple copies of the Fc binding domain of Protein G, or protein A, protein A-G fusions, or Fc-receptors (FcR) to the external medium.

15. The drug delivery system according to claim 14, wherein the Fc binding domain of Protein G is anchored to the outer membrane of the nanocells via an invasin protein fragment covering amino acids 1-796 of *Yersinia pseudotuberculosis*.

16. The drug delivery system according to claim 14, wherein the nanocells are produced from lipid A minus bacterial strains.

17. The drug delivery system according to claim 14, wherein the Fc binding domain of Protein G is a polypeptide fragment containing amino acids 191-384 of Streptococcal Protein G.

18. The drug delivery system according to claim 14, wherein the nanocells are coated with binding molecules that bind to antigens that have therapeutic or diagnostic properties.

19. The drug delivery system according to claim 14 for use in therapy, diagnosis or theranosis.

20. A method for delivery of a biological system to target cells, comprising the steps of
producing the biological system of claim 1 in a nanocell parental bacterial strain and producing nanocells from said biological system-producing parental bacteria cells, or incubating the biological system with nanocells produced from parental bacteria cells,
coating the nanocells with one or more antibodies that recognize antigens specifically expressed by said target cells by exposing multiple copies of the Fc binding domain of protein G to the external medium,
exposing the target cells to said nanocells.

* * * * *